United States Patent
Chung et al.

(10) Patent No.: US 9,867,886 B2
(45) Date of Patent: Jan. 16, 2018

(54) COMPLEX IN WHICH ANTI-COTININE ANTIBODY IS BOUND TO CONJUGATE OF COTININE AND BINDING SUBSTANCE, AND USE THEREOF

(75) Inventors: Junho Chung, Seongnam-si (KR); Sunyoung Park, Seoul (KR); Do Been Hwang, Seoul (KR); Hwa Kyoung Lee, Suncheon-si (KR)

(73) Assignee: SNU R&DB FOUNDATION, Seoul (KR)

( * ) Notice: Subject to any disclaimer, the term of this patent is extended or adjusted under 35 U.S.C. 154(b) by 630 days.

(21) Appl. No.: 14/111,133

(22) PCT Filed: Apr. 16, 2012

(86) PCT No.: PCT/KR2012/002873
§ 371 (c)(1),
(2), (4) Date: Nov. 11, 2013

(87) PCT Pub. No.: WO2012/141554
PCT Pub. Date: Oct. 18, 2012

(65) Prior Publication Data
US 2014/0056926 A1 Feb. 27, 2014

Related U.S. Application Data

(60) Provisional application No. 61/476,018, filed on Apr. 15, 2011.

(51) Int. Cl.
| | |
|---|---|
| C07K 16/44 | (2006.01) |
| G01N 33/94 | (2006.01) |
| B82Y 5/00 | (2011.01) |
| A61K 47/48 | (2006.01) |
| C07D 401/04 | (2006.01) |
| C07D 401/14 | (2006.01) |
| A61K 31/465 | (2006.01) |
| C07K 16/28 | (2006.01) |
| A61K 39/00 | (2006.01) |
| C07K 16/18 | (2006.01) |

(52) U.S. Cl.
CPC ...... *A61K 47/48715* (2013.01); *A61K 31/465* (2013.01); *A61K 47/48061* (2013.01); *A61K 47/48723* (2013.01); *B82Y 5/00* (2013.01); *C07D 401/04* (2013.01); *C07D 401/14* (2013.01); *C07K 16/2848* (2013.01); *C07K 16/44* (2013.01); *G01N 33/94* (2013.01); *A61K 2039/505* (2013.01); *C07K 16/18* (2013.01); *C07K 2317/24* (2013.01); *C07K 2317/31* (2013.01); *C07K 2317/622* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 2008/0226650 A1 | 9/2008 | Park et al. | |
| 2012/0065243 A1* | 3/2012 | Woolf | C12N 15/111 514/44 A |
| 2012/0082616 A1* | 4/2012 | Trawick | A61K 9/1271 424/1.21 |

FOREIGN PATENT DOCUMENTS

EP 0194158 A2 9/1986

OTHER PUBLICATIONS

European Patent Office, Communication dated Oct. 10, 2014 issued in corresponding European application No. 12772034.0.
Park et al, "A sensitive enzyme immunoassay for measuring cotinine in passive smokers," Elsevier, Clinica Chimica Acta, 2010, pp. 1238-1242 (5 total pages).
Korean Intellectual Property Office; Communication dated Jun. 6, 2017, in counterpart Korean application No. 10-2016-0066454.
Zhiqiang An , et al., "IgG2m4, an engineered antibody isotype with reduced Fc function", mAbs, vol. 1, Issue 6, 2009, pp. 572-579.

* cited by examiner

*Primary Examiner* — Benjamin P Blumel
(74) *Attorney, Agent, or Firm* — Sughrue Mion, PLLC

(57) ABSTRACT

The present invention relates to a complex in which an anti-cotinine antibody is bound to a conjugate of a binding material and cotinine, and a use of the complex. The complex according to the present invention may be used as an analysis tool in an in vitro biological assay method, and may retain the specific reactivity and the biological function of the binding material, and the capabilities of inducing complement-mediated cell cytotoxicity (CDC) and antibody-dependent cell cytotoxicity (ADCC) and a prolonged in vivo half-life, which are intrinsic characteristics of an antibody.

4 Claims, 21 Drawing Sheets

Cotinine    PEG linker    WKYMVm-NH$_2$

Cotinine  PEG linker  AS1411         Cotinine  PEG linker  Pegaptanib

COMPLEX IN WHICH ANTI-COTININE ANTIBODY IS BOUND TO CONJUGATE OF COTININE AND BINDING SUBSTANCE, AND USE THEREOF

CROSS REFERENCE TO RELATED APPLICATIONS

This application is a National Stage of International Application No. PCT/KR2012/002873 filed Apr. 16, 2012, claiming priority based on Unites States Provisional Application No. 61/476,018 filed Apr. 15, 2011, the contents of all of which are incorporated herein by reference in their entirety.

FIELD OF THE INVENTION

The present invention relates to a complex in which an anti-cotinine antibody is bound to a conjugate of a binding material and cotinine, and a use of the complex.

BACKGROUND OF THE INVENTION

While numerous peptide and aptamer biological drugs have promising properties as a drug candidate, it is known that the in vivo half-life of the biological drugs is short and ranges, for example, from several minutes to several hours since the biological drugs are easily degraded in the body by peptidase and nuclease, etc., or rapidly excreted through the kidneys (Sato A. K. et al., *Curr Opin Biotechnol*, 17, 638-642, 2006). To resolve the problem of instability and short sustain time of drug efficacy, a technique has been employed, wherein polyethylene glycol (PEG) is conjugated to the biological drugs (Veronese, F. M. & Pasut G., *Drug Discov Today*, 10, 1451-1458, 2005) to inhibit degradation by an in vivo enzyme and repress uptake by the kidneys and blood vessels, thereby extending retention time in blood of the drugs. However, such pegylation is problematic in that it takes a long time and requires specific optimizations depending on a binding material, and various molecular conjugates may also be produced due to the heterogeneous binding of the PEG molecules.

For the purpose of being used as a novel delivery platform, a hapten should meet the requirements of being nontoxic to animals and humans and not having physiological activity. Cotinine is a major metabolite of nicotine to which humankind has been exposed for a long time. Thus, cotinine is a hapten that is suitable as a novel delivery platform application. Also, cotinine is a relatively very stable material having $LD_{50}$ of about 2-4 g/kg in a mouse (Riah O. et al., *Toxicol. Lett.*, 109, 21-29, 1999), and no particular side effects have not been reported even in the 4-day administration at a daily dose of 1.8 g of cotinine (Bowman, E. R. & Mc, K. H., Jr., *J. Pharmacol. Exp. Ther.*, 135, 306-311, 1962). Also, a metabolic process of cotinine in mammals has been clearly revealed, and the fact that the half-life of cotinine in serum is about 16 hours is also well known (Benowitz N. L. et al., *3rd Handb. Exp. Pharmacol.*, 29-60, 2009). In addition, cotinine does not exhibit physiological activity in humans, and any physiological and behavioral changes have not been reported even in the case of maximally uptaking 160 mg of cotinine for three days (Hatsukami, D. K. et al., *Pharmacol. Biochem. Behav.*, 57, 643-650, 1997).

Meanwhile, aptamers have been used for various analyses and experiments, since they can be specifically folded in a three dimensional form, thereby being capable of binding to a target with high-affinity and specificity, similarly to an antibody. The conventional methods for preparing a complex with an antibody using an aptamer are mainly achieved by conjugating the aptamer to biotin or digoxigenin and then allowing the resulting conjugate to form a complex with avidin or an anti-digoxigenin antibody.

The present inventors have prepared a complex in which an anti-cotinine antibody is bound to a conjugate of a binding material and cotinine by using cotinine as a hapten, and have accomplished the present invention by finding out that the complex may retain the specific reactivity and the biological function of the binding material, and the capabilities of inducing complement-mediated cell cytotoxicity (CDC), antibody-dependent cell cytotoxicity (ADCC), and a prolonged in vivo half-life, which are intrinsic characteristics of an antibody.

SUMMARY OF THE INVENTION

Accordingly, it is an object of the present invention to provide a complex in which an anti-cotinine antibody is bound to a conjugate of cotinine and a binding material.

It is another object of the present invention to provide an in vitro biological assay method which is characterized by using a conjugate of cotinine and a binding material as an analysis tool.

It is still another object of the present invention to provide a method for increasing in vivo half-life of a binding material by binding an anti-cotinine antibody to a conjugate in which the binding material is conjugated to cotinine.

It is still another object of the present invention to provide a method of inducing complement-mediated cell cytotoxicity (CDC) against a cell to which a binding material is bound, by binding an anti-cotinine antibody to a conjugate in which the binding material is conjugated to cotinine.

It is still another object of the present invention to provide a method of inducing antibody-dependent cell cytotoxicity (ADCC) against a cell to which a binding material is bound, by binding an anti-cotinine antibody to a conjugate in which the binding material is conjugated to cotinine.

It is still another object of the present invention to provide a method of changing body distribution of a binding material to a general body distribution pattern of an antibody, by binding an anti-cotinine antibody to a conjugate in which the binding material is conjugated to cotinine.

In accordance with one object of the present invention, there is provided a complex in which an anti-cotinine antibody is bound to a conjugate of cotinine and a binding material.

In accordance with another object of the present invention, there is provided an in vitro biological assay method which is characterized by using a conjugate of cotinine and a binding material as an analysis tool.

In accordance with still another object of the present invention, there is provided a method for increasing in vivo half-life of a binding material by binding an anti-cotinine antibody to a conjugate in which the binding material is conjugated to cotinine.

In accordance with still another object of the present invention, there is provided a method of inducing complement-mediated cell cytotoxicity (CDC) against a cell to which a binding material is bound, by binding an anti-cotinine antibody to a conjugate in which the binding material is conjugated to cotinine.

In accordance with still another object of the present invention, there is provided a method of inducing antibody-dependent cell cytotoxicity (ADCC) against a cell to which a binding material is bound, by binding an anti-cotinine antibody to a conjugate in which the binding material is conjugated to cotinine.

In accordance with still another object of the present invention, there is provided a method of changing body distribution of a binding material to a general body distribution pattern of an antibody, by binding an anti-cotinine antibody to a conjugate in which the binding material is conjugated to cotinine.

BRIEF DESCRIPTION OF THE DRAWINGS

The above mentioned and other objects, and characteristic of the present invention will be apparent from following detailed description of the present invention together with accompanying drawings.

DETAILED DESCRIPTION OF THE INVENTION

Hereinafter, the present invention will be described in more detail.

As used herein, the term "antibody" means a material which is produced by antigen stimulation in an immune system, and the type of the antibody is not particularly limited. In the present invention, the antibody includes an animal antibody, a chimeric antibody, a humanized antibody or a complete human antibody. Also, in the present invention, the antibody includes a fragment of the antibody (e.g., Fab) retaining antigen binding ability.

As used herein, the term "chimeric antibody" refers to an antibody, wherein variable regions of an antibody or complementarity-determining regions (CDRs) thereof are derived from a first animal, and other parts of the antibody are derived from a different animal. Such antibody, for example, may be an antibody having variable regions of the antibody which is derived from an animal other than a human (e.g., a mouse, a rabbit, and poultry), and constant regions of the antibody which is derived from a human. Such chimeric antibody may be prepared by using a known method in the art such as a gene recombination, etc.

As used herein, the term "heavy chain" refers to both a full length heavy chain and a fragment thereof, wherein the full length heavy chain includes a variable region domain $V_H$ having an amino acid sequence which is sufficient for imposing specificity to an antigen, and three constant domains, CH1, CH2, and CH3.

As used herein, the term "light chain" refers to both a full length light chain and a fragment thereof, wherein the full length light chain includes a variable region domain $V_L$ having an amino acid sequence which is sufficient for imposing specificity to an antigen, and a constant domain $C_L$.

As used herein, the term "complementarity-determining region" refers to a site which imposes binding specificity for an antigen in the variable regions of an antibody.

As used herein, the term "conjugate" means a heterologous molecule and may be produced by covalently attaching one or more polypeptide(s), typically one polypeptide, to one or more non-polypeptide part(s), particularly a polymer part, such as a polymer molecule, a lipophilic compound, a carbohydrate part, and an organic derivatizing agent. In addition, conjugate(s) can be attached to the one or more carbohydrate part(s), particularly by using N- or O-glycosylation. Covalent attachment means that a polypeptide and a non-polypeptide part are covalently bound each other directly or covalently linked to each other indirectly via a linking bridge, a space, a linking part, or a mediating part, etc. For example, a conjugate disclosed herein in which a binding material is conjugated with cotinine is included in the present definition.

Figure 22:
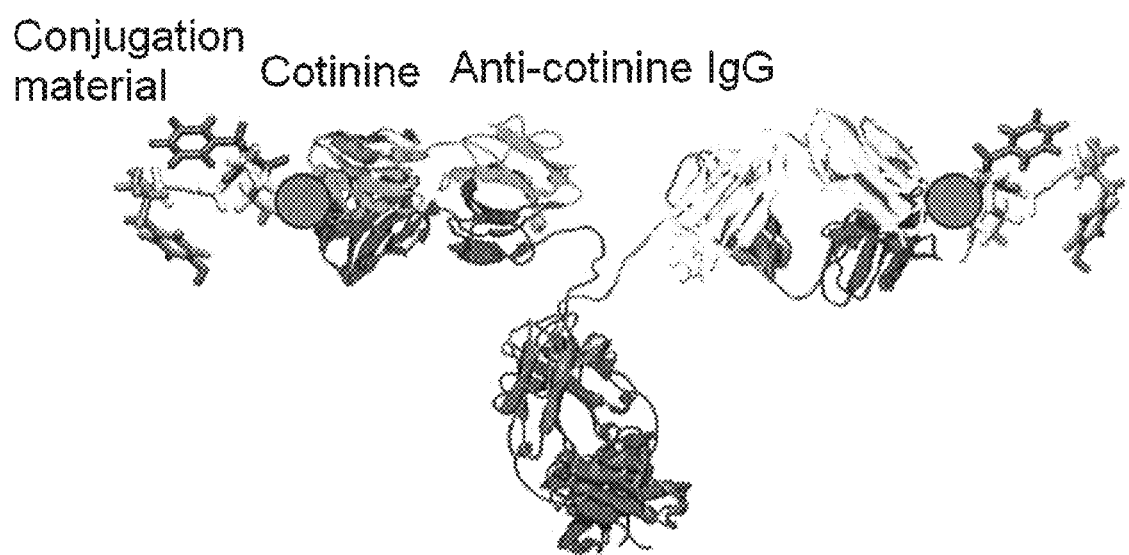
FIG. 22 shows a complex in which the anti-cotinine antibody is bound to a conjugate of a binding material and cotinine.

The present invention provides a complex in which an anti-cotinine antibody is bound to a conjugate of a binding material and cotinine (FIG. 22).

Also, the present invention provides an in vitro biological assay method characterized by using the conjugate of cotinine and a binding material as an analysis tool. The in vitro biological assay method is characterized by being selected from the group consisting of a flow cytometry, a western blot analysis, an immunoprecipitation assay, and an enzyme-linked immunochemical assay.

According to the present invention, the complex in which the anti-cotinine antibody is bound to the conjugate of the binding material and cotinine may retain inherent properties of both of the binding material and the antibody owing to the use of cotinine as a hapten. Specifically, the complex may retain specific reactivity and a function of a molecule; capabilities of inducing complement-mediated cell cytotoxicity (CDC), and antibody-dependent cell cytotoxicity (ADCC), which are characteristics of an antibody; and a prolonged in vivo half-life.

Therefore, the present invention provides a method for increasing an in vivo half-life of a binding material, which comprises binding an anti-cotinine antibody to a conjugate in which the binding material is conjugated with cotinine.

Also, the present invention provides a method of inducing CDC against a cell to which a binding material is bound, by binding the anti-cotinine antibody to the conjugate in which the binding material is conjugated with cotinine.

Also, the present invention provides a method of inducing ADCC against a cell to which the binding material is bound, by binding the anti-cotinine antibody to the conjugate in which the binding material is conjugated with cotinine.

Also, the present invention provides a method of changing body distribution of a binding material to a general body distribution pattern of an antibody, by binding the anti-cotinine antibody to the conjugate in which the binding material is conjugated with cotinine.

Since the complex according to the present invention has one kind of antibody and cotinine, the complex can be prepared by simply conjugating a binding material having a short sequence to cotinine, thereby acting as a delivery platform which is highly intensive, easy to develop, and of a simple form.

Thus, the complex according to the present invention is a novel antibody of which antigenic reactivity is determined by a binding material conjugated to cotinine, and may be used as a therapeutical antibody exhibiting inherent biological and chemical functions of the molecules.

Cotinine is a major metabolic product of nicotine, a major ingredient of tobacco smoke, and it is known as a considerably stable molecule since a very little immediate toxicity has been reported so far, although human are exposed to tobacco smoke for a long time. A relative non-toxic property of cotinine makes cotinine to become an ideal conjugate for a molecule to be used in vivo. In the present invention, a short half-life of a binding material may be increased remarkably by conjugating cotinine with the binding material.

As used herein, the term "binding material" may refer to various biological and chemical materials exhibiting particular therapeutic activity or binding reactivity etc.

The binding material may be selected, for example, from the group consisting of a peptide, an aptamer, a hormone, a protein and a chemical material, and preferably selected from the group consisting of WKYMVm-NH$_2$ peptide (WKYMVm-NH$_2$), wkymvm-NH$_2$ peptide (wkymvm-NH$_2$), AS1411 aptamer, pegaptanib, abciximab and insulin.

Abciximab (ReoPro), which may be used as a binding material in the present invention, is a mouse/human chimeric Fab exhibiting reactivity to integrin alpha2b beta3, which is broadly expressed on the surface of a platelet.

According to an aspect of the present invention, a complex, which includes the anti-cotinine antibody and a cotinine-abciximab conjugate prepared by conjugating abciximab with cotinine (hereinafter, cotinine-abciximab/anti-cotinine antibody complex), is prepared, and the complex maintains a substantially the same level of reactivity as abciximab to integrin alpha2b beta3 and platelet (see Experimental Example 9, FIGS. 18 and 19).

Insulin, which may be used as a binding material in the present invention, is an important hormone to regulate in vivo metabolism of carbohydrate and lipid. Insulin has two kinds of polypeptide chains, and has one intra-molecular disulfide bond in A chain consisting of 21 amino acid resides and two inter-molecular disulfide bonds which link A chain to B chain consisting of 30 amino acid residues (see Nicol D S, Smith, L F., *Nature.* 1960 Aug. 6, 187:483-5, PubMed PMID: 14426955).

According to an aspect of the present invention, a complex, which includes the anti-cotinine antibody and a cotinine-insulin conjugate prepared by conjugating insulin with cotinine (hereinafter, a cotinine-insulin/anti-cotinine antibody complex), is prepared, and the complex maintains binding ability of insulin to a cell expressing an insulin receptor (see Experimental Example 10, FIGS. 20 and 21).

WKYMVm-NH$_2$ peptide, which may be used as a binding material in the present invention, is an anti-septicemia therapeutic peptide and an agonist of formyl peptide receptors (FPR). WKYMVm-NH$_2$ peptide serves an antibiotic action by inducing chemotactic migration of phagocytes and increasing superoxide generation of monocytes and neutrophils.

Figure 2:
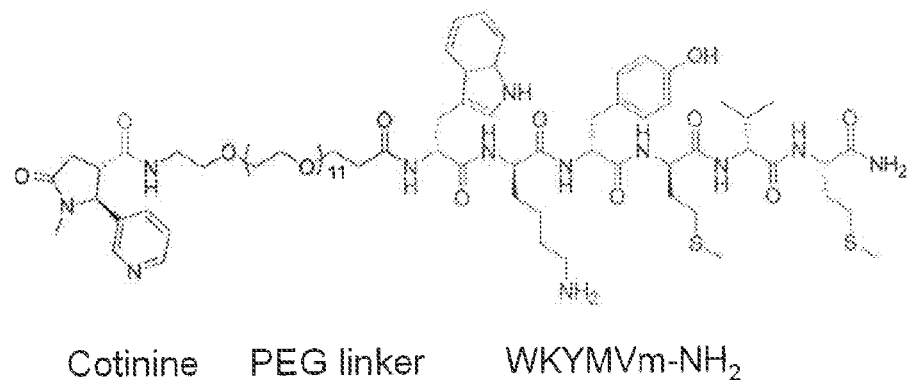
FIGS. 2 and 3 show structural formulae of a cotinin-WKYMVm-NH$_2$ conjugate, which is synthesized in Example 3-1, and a cotinin-AS1411 conjugate and a cotinine-pegaptanib conjugate, which are synthesized in Example 3-2.

According to an aspect of the present invention, a complex, which includes the anti-cotinine antibody and a cotinine-WKYMVm-NH$_2$ conjugate prepared by conjugating WKYMVm-NH$_2$ peptide with cotinine (FIG. 2) (hereinafter, a cotinine-WKYMVm-NH$_2$/anti-cotinine antibody complex), is prepared. Specifically, the WKYMVm-NH$_2$ peptide (see publications [Baek S H, et al., *J Biol. Chem.,* 1996 Apr. 5; 271(14):8170-5. PubMed PMID: 8626507]; and [Kim S D, et al., *J. Immunol.* 2009 Nov. 1, 183(9): 5511-7. PubMed PMID: 19843937]) is attached to cotinine using PEG (mini-PEG) as a linker. Then, the conjugate is subjected to form a complex with an anti-cotinine antibody (Park S, et al., *Clin Chim Acta.* 2010 Sep. 6, 411(17-18): 1238-42. Epub 2010 May 11. PubMed PMID: 20438723).

Figure 5:
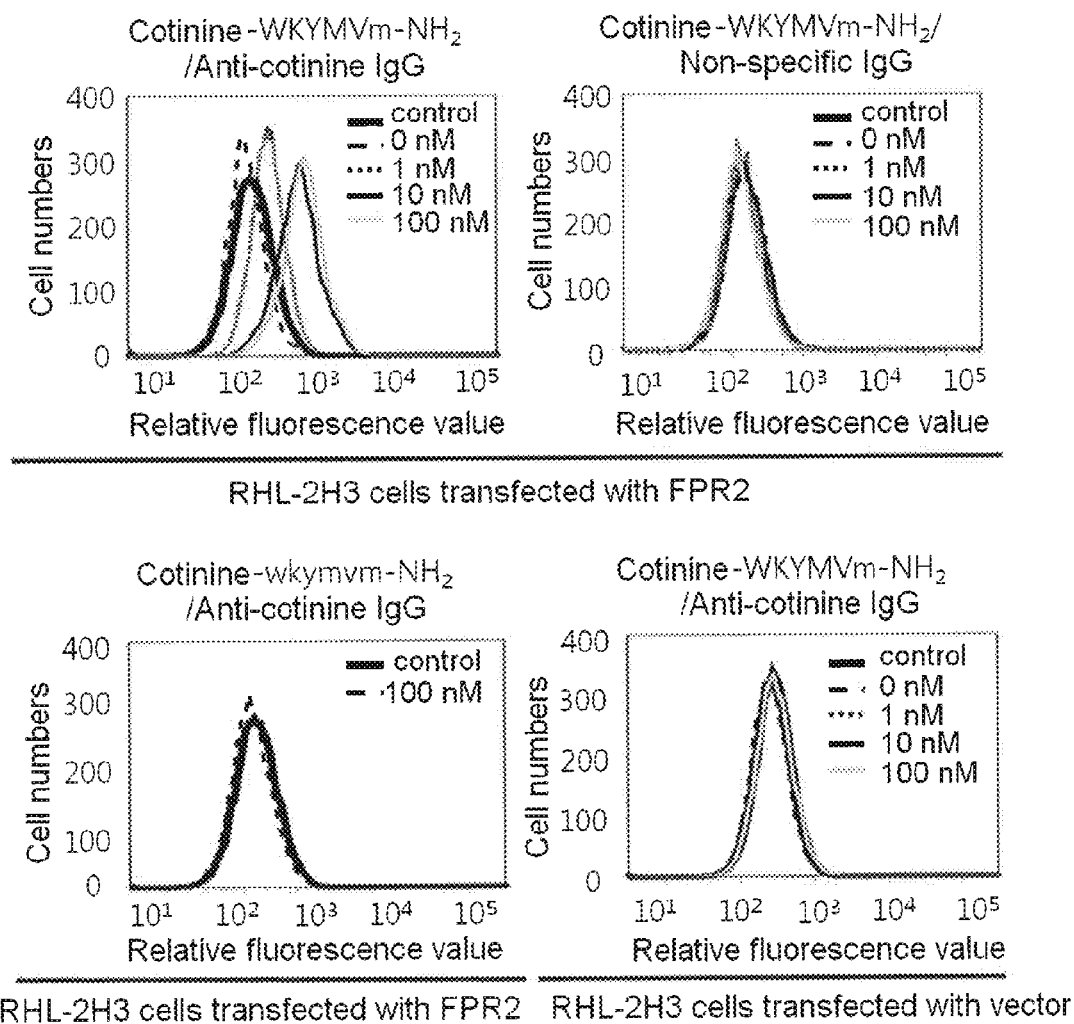
FIG. 5 is a graph showing a specific binding ability of a cotinine-WKYMVm-NH$_2$/anti-cotinine IgG complex to a FPR2 cell receptor.

The complex thus produced in accordance with the present invention exhibits reactivity to a cell expressing a formyl peptide receptor in a flow cytometry analysis, and thus it can be understood that binding ability of WKYMVm-NH$_2$ is conserved (see FIG. 5). Also, a biological function of WKYMVm-NH$_2$ is maintained after conjugation with cotinine, since the cotinine-WKYMVm-NH$_2$ conjugate successfully releases calcium from a cell (see FIGS. 6 to 8). In addition, in a septicemia mouse model, a mouse administered with the cotinine-WKYMVm-NH$_2$/anti-cotinine antibody complex was recovered from septicemia in a dose-dependent manner, while a mouse administered with the cotinine-WKYMVm-NH$_2$ conjugate only did not exhibited a therapeutic effect. Such results indicate that a biological therapeutic effect of the WKYMVm-NH$_2$ peptide is maintained in the complex, as well as, the half-life of the cotinine-WKYMVm-NH$_2$ conjugate is extended due to the long in vivo half-life of the anti-cotinine antibody (see FIG. 9).

Pegaptanib, which may be used as a binding material in the present invention, is a pegylated anti-VEGF aptamer binding to VEGF 165 which plays an important role in angiogenesis.

Figure 3:
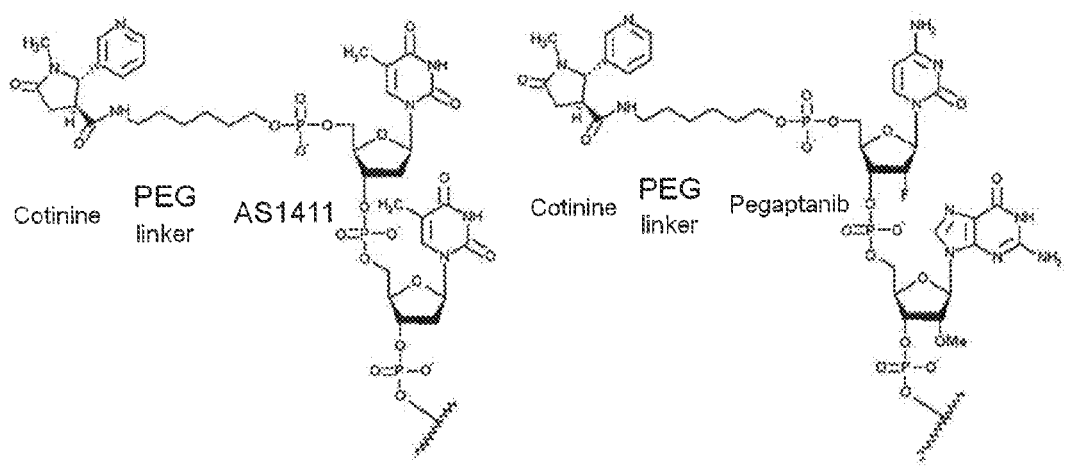

According to an aspect of the present invention, a complex, which includes the anti-cotinine antibody and a cotinine-pegaptanib conjugate prepared by conjugating a nucleic acid part of pegaptanib with cotinine (see FIG. 3) (hereinafter, a cotinine-pegaptanib/anti-cotinine antibody complex), is prepared, and the complex has a considerably improved in vivo half-life (see Experimental Example 7).

AS1411 aptamer, which may be used as a binding material in the present invention, is a G-rich oligonucleotide and is characterized by binding to nucleolin, which is expressed on the surface of a cancer cell, to be absorbed into a cancer cell, thereby destroying a normal function of nucleolin such as DNA replication and cell proliferation.

A stable complex of an aptamer with an antibody may be formed in the present invention by conjugating cotinine to 5'-end of the aptamer. According to an aspect of the present invention, a complex, which includes the anti-cotinine antibody and a cotinine-AS1411 conjugate prepared by conjugating the AS1411 with cotinine (see FIG. 3) (hereinafter, a cotinine-AS1411/anti-cotinine antibody complex), is prepared, and the complex maintains binding ability to VEGF, as AS1411 aptamer (see Experimental Example 8).

The binding material of the present invention is characterized by being linked to cotinine via a PEG linker (mini PEG-12) or an amino C6 linker.

The conjugate of cotinine and the binding material forms the complex of the present invention by binding to the anti-cotinine antibody, wherein the conjugate may bind to a heavy chain or a light chain of the antibody, and preferably to an antigen binding site of the anti-cotinine antibody.

Meanwhile, an antibody, which is prepared and expressed in an IgG form by employing a high-affinity anti-cotinine Fab (see U.S. Pat. No. 8,008,448), may be used as the anti-cotinine antibody of the present invention.

For example, the anti-cotinine antibody may be prepared in the following manner. A light chain gene and a heavy chain gene, which are prepared by modifying the method disclosed in the U.S. Pat. No. 8,008,448, are inserted into an expression vector (e.g., pcDNA3.1), respectively. Subsequently, the anti-cotinine IgG antibody according to the present invention may be obtained by transforming a mammalian cell with the vectors to express an antibody protein, then purifying the culture by using a conventional method.

In this case, a CHO DG 44 cell (Invitrogen, USA) may be used as the mammalian cell and a purification method using protein A column (Repligen, USA) after concentrating the culture is preferable.

According to the present invention, the anti-cotinine antibody is selected from the group consisting of: the antibody; an antibody fragment selected from Fab, ScFv and a domain antibody; and a fusion protein comprising the antibody or the antibody fragment as a component.

A complex in which the anti-cotinine antibody is bound to a conjugate of a binding material and cotinine may be prepared according to the method, which comprise the steps of: 1) preparing a conjugate in which a binding material is conjugated with cotinine; 2) preparing the anti-cotinine antibody; and 3) binding the anti-cotinine antibody and the conjugates in which the binding material is conjugated with cotinine.

Specifically, the method may comprise the steps of: a) inserting a nucleic acid molecule coding a complex in which the anti-cotinine antibody is bound to a conjugate of a binding material and cotinine; b) introducing the vector into a host cell; and c) culturing the host cell.

Preparing the complex in which the anti-cotinine antibody is bound to a conjugate of a binding material and cotinine may be a useful method for producing a therapeutical antibody in the case of setting an anti-cotinine antibody production system in a clinical phase. It takes considerable time for development of de novo therapeutical antibody, however a therapeutical antibody in a small molecule form, which may be synthesized rapidly and easily in a high-throughput manner in a clinical phase, may be prepared by using the method of preparing a complex of the present invention.

According to the present invention, after conjugating cotinine with a binding material, a complex is formed by binding the anti-cotinine antibody to the prepared conjugate. Antigen reactivity of the antibody may be produced by the binding material which conjugates to cotinine. The complex thus prepared, according to the present invention, maintains all characteristics of the antibody including CDC, ADCC and a prolonged in vivo half-life.

Compared to an existing molecule-antibody conjugate in which a conjugation molecule is directly bound to an antibody, the complex of the present invention is expected to exhibit further advantages in an immunological aspect.

Specifically, the existing conjugate of a therapeutical molecule and an antibody may be used as a hapten-carrier, and an immunological reaction may be triggered immediately against a molecule which is directly bound to the antibody. When the molecule-antibody conjugate is surrounded by antigen presenting cells, the antibody will be degraded into short peptides. Under this circumstance, numerous therapeutical molecules will still be chemically cross-linked to the short peptides. If one of the peptides, which are linked to the therapeutical molecule, has high affinity to a particular MHC molecule, the peptide will be presented well on a surface of an antigen presenting cell. This will efficiently induce cellular immunity to the therapeutical molecule.

However, in the case of the complex of the present invention, when the complex is surrounded by antigen presenting cells, the antibody is degraded into short peptides, and thus the conjugate of cotinine and the binding material will be separated from the anti-cotinine antibody immediately. This can serve as an advantage since it makes difficult to develop immunogenicity to the therapeutical molecule bounded to cotinine.

Hereinafter, the present invention will be described in more detail with the following examples. However, these are provided only for illustration purposes, and are not intended to limit the scope of the present invention.

Example 1: Preparation of Gene of Anti-Cotinine Rabbit/Human Chimeric IgG (1-1) Amplification of Antibody Variable Region from Anti-Cotinine Rabbit scFv To amplify an antibody variable region ($V_L$ and $V_H$) of a rabbit, a polymerase chain reaction (PCR) was performed using an anti-cotinine rabbit scFv gene (see U.S. Pat. No. 8,008,448), as a template, 60 pmole of forward and reverse primers (SEQ ID NOs: 11 and 12) for $V_L$, respectively, and 60 pmole of forward and reverse primers (SEQ ID NOs: 13 and 14) for $V_H$, respectively.

Specifically, to perform a PCR reaction, 1 μL of cDNA (about 0.5 μg) which was synthesized in U.S. Pat. No. 8,008,448, 60 pmol of a forward primer and a reverse primer, respectively, 10 µL of 10×PCR buffer, 8 µL of 2.5 mM dNTP mixture, and 0.5 µL of Taq polymerase were mixed, and then, 100 µL of distilled water was added thereto. The resultant mixture was denatured at 94° C. for 10 minutes, proceeded with 30 thermal cycles of 94° C. for 15 seconds, 56° C. for 30 seconds and 72° C. for 90 seconds, followed by final elongation at 72° C. for 10 minutes.

The amplified DNA thus obtained was subjected to electrophoresis on 1% agarose gel, and then purified using a QIAquick gel extraction kit (Qiagen, USA).

(1-2) Amplification of Antibody Constant Region of Human

To amplify antibody constant regions of a human light chain constant region (Cκ) and a human heavy chain constant region (CH1-CH3), PCR was performed by using the same method in the Example (1-1) except that 20 ng of pComb3×TT vector (Barbas et al., *Proc. Natl. Acad. Sci.*, USA, (1991), 15:88(18), 7978-7982) was used as a template, and 60 pmole of forward and reverse primers for Cκ (SEQ ID NOs: 15 and 16) and forward and reverse primers for CH1-CH3 (SEQ ID NOs: 17 and 18), were used, respectively. Then, the amplified DNA was subjected to gel-electrophoresis, followed by purification.

(1-3) Amplification of Light Chain

To perform PCR for amplifying a light chain, a light chain gene was prepared by binding the light chain variable region ($V_L$) of a rabbit antibody and the light chain constant region (Cκ) of a human antibody, which were prepared and purified in Examples (1-1) and (1-2), through overlap extension PCR.

Specifically, PCR was performed using the same method in the example (1-1) except that 100 ng of $V_L$, 100 ng of Cκ PCR products, and 60 pmole of forward and reverse primers for a light chain of an anti-cotinine rabbit/human chimeric antibody (SEQ ID NOs: 7 and 8), respectively, were used for the PCR reaction. Then, the amplified DNA was subjected to agarose gel electrophoresis and purified using the same method in Example (1-1).

(1-4) Amplification of Heavy Chain

To perform PCR for amplifying a heavy chain, a heavy chain gene was prepared by binding the heavy chain variable region ($V_H$) of a rabbit antibody and the heavy chain constant region (CH1-CH3) of human antibody, which were prepared and purified in Examples (1-1) and (1-2) through overlap extension PCR.

Specifically, for performing PCR reaction, 100 ng of $V_H$, 100 ng CH1-CH3 PCR products, 60 pmole of forward and reverse primers for a heavy chain of the anti-cotinine rabbit/human chimeric antibody (SEQ ID NOs: 9 and 10), respectively, 10 µL 10×PCR buffer, 8 µL 2.5 mM dNTP mixture and 0.5 µL Taq polymerase were mixed, and then 100 µL of distilled water was added thereto. The mixture was denatured at 94° C. for 10 minutes, proceeded with 20 thermal cycles of 94° C. for 15 seconds, 56° C. for 30 seconds and 72° C. for 180 seconds, followed by final elongation at 72° C. for 10 minutes.

Then, the amplified DNA was subjected to agarose gel electrophoresis and purified using the same method in Example (1-1).

(1-5) Construction of Expression Vector Including Gene of Anti-Cotinine Rabbit/Human Chimeric IgG The light chain PCR products which were prepared and purified in Example (1-3), and the heavy chain PCR products which were prepared and purified in Example (1-4) were digested with restriction enzymes HindIII/XbaI (NEB, USA) and restriction enzymes BamHI/NheI (NEB, USA), respectively, then isolated and inserted into a multiple cloning site (MCS) of an expression vector (pcDNA3.1).

Example 2: Expression and Purification for In Vitro Analysis of Anti-Cotinine Rabbit/Human Chimeric IgG A mammalian cell, CHO DG 44 (Invitrogen, USA), was transfected with an expression vector DNA including an anti-cotinine rabbit/human chimeric IgG gene. The transfected cell was cultured in a condition of 37° C. and 135 rpm in CD OptiCHO™ expression medium (GIBCO), including 100 U/mL of penicillin and 100 g/mL of streptomycin (GIBCO, USA), to which 500 µg/mL of G418 was added. The supernatant of the culture medium was concentrated through Labscale TFF system (Millipore, USA), and then purified with a protein A column (Repligen Co., USA). The purified IgG of 150 KDa was determined by Coomassie staining (see FIG. 1) and used in a subsequent experiment (Experimental Example).

Figure 1:
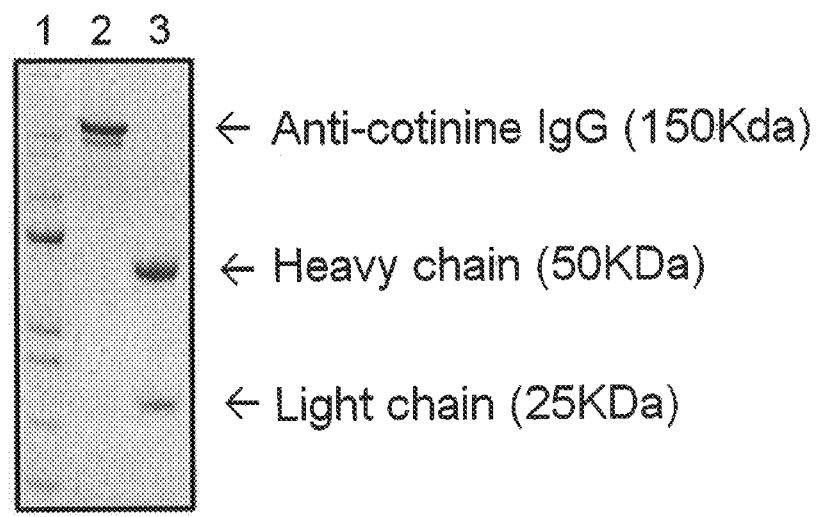
FIG. 1 is a photograph showing a gel obtained by performing Coomassie staining on an anti-cotinine antibody which is purified in Example 2.

As shown in FIG. 1, it could be understood that lane 1 shows a size marker, lane 2 shows unreduced anti-cotinine IgG (150 KDa), and lane 3 shows a light chain (25 KDa) and a heavy chain (50 KDa) which were as reduced anti-cotinine IgG.

Example 3: Preparation of Conjugate of Cotinine and Binding Material (3-1) Conjugate of Cotinine and Peptide A WKYMVm-NH$_2$ peptide (WKYMVm-NH$_2$, SEQ ID NO: 1) and a wkymvm-NH$_2$ peptide (wkymvm-NH$_2$, SEQ ID NO: 2) were used as peptides. WKYMVm-NH$_2$ and wkymvm-NH$_2$ were synthesized in an ASP48S automatic peptide synthesizer by a solid phase peptide synthesis method. Then, the peptides were purified through reverse phase HPLC using Vydac Everest C18 column (250 mm×22 mm, 10 µm) (>95% purity), and the size of peptides were determined through LC/MS (Agilent HP1100 series) (>95% purity).

Meanwhile, cotinine-WKYMVm-NH$_2$ and cotinine-wkymvm-NH$_2$, which were conjugates of cotinine and a peptide, were synthesized by performing the same method as above except that a PEG linker and cotinine were introduced at the last process for synthesizing a peptide.

A method for preparing the conjugate of cotinine and a peptide was performed according to the following steps of: firstly synthesizing a basic peptide using ASP48S automatic peptide synthesizer; adding Fmoc-m-OH (8 equivalents), which is a first sequence, and a coupling agent HBTU (8 equivalents)/HOBt (8 equivalents)/NMM (16 equivalents) dissolved in DMF, in a MBHA link amide resin for C-terminal amidation; and reacting the resultant mixture for 2 hours at a room temperature. Subsequently, 20% of piperidine in DMF was added to the mixture and then reacted two times for 5 minutes at a room temperature to degrade Fmoc. The process was repeated to produce a backbone of a peptide, NH$_2$—W(Boc)-K(Boc)-Y(tBu)-M-V-m-MBHA, linked amide resin, and then taking a small amount of peptide is bound to the resins. Cleavage cocktail (TFA/TIS/H$_2$O=95/2.5/2.5) was added to the taken resin to separate a peptide from the resin, and the peptide was precipitated by adding an excess amount of diethyl ether. Small amount of crude peptides thus obtained was dissolved in DW/CAN(1/1) to determine the a molecular weight of a desired peptide to synthesize (WKYMVm-NH$_2$) by LC/MS, and then Fmoc-mini PEG12-OH was coupled by the same process as above.

Then, the resin was taken again and a molecular weight was determined through LC/MS. Trans-4-cotinine carboxylic acid was subjected to coupling reaction again using the same process as above, and then the peptide was separated from the resin by adding cleavage cocktail (TFA/TIS/H$_2$O=95/2.5/2.5). Then, the peptide was precipitated by adding an excess amount of diethyl ether and purified through HPLC. After that, the peptide was freeze-dried after determining a molecular weight by LC/MS.

WKYMVm-NH$_2$ and wkymvm-NH$_2$ peptides, and cotinine-peptide conjugates, which were synthesized by the above process, were dissolved in DMSO and stored at −20° C. A structure of the cotinine-WKYMVm-NH$_2$ conjugate thus prepared was shown in FIG. 2.

(3-2) Conjugate of Cotinine and Aptamer

An AS1411 DNA aptamer (5'-dTTGGTGGTGGTGGTT-GTGGTGGTGGTGG-3', SEQ ID NO: 3), a CR026 DNA aptamer (5'-dCCTCCTCCTCCTTCTCCTCCTCCTCC-3', SEQ ID NO: 4), and a pegaptanib RNA aptamer (5'-pCfpGmpGmpArpArpUfpCfpAmpGmpUfpGmpAmpAm-pUfpGmpCfpUfpUfp AmpUfpAmpCfpAmpUfpCfpCf-pGm3'-p-dT-3, SEQ ID NO: 5) were used as aptamers.

Meanwhile, cotinine-AS1411, cotinine-CR026 and cotinine-pegaptanib, as conjugates of cotinine and an aptamer, were synthesized in a 3' to 5' in an oligonucleotide synthesizer through solid phase oligonucleotide synthesis method, and an amino C6 linker (ST Pharm, Korea) was attached at the last process of synthesis. Then, the conjugate was purified (>95% purity) by reversed-phase high-pressure liquid chromatography using a Xbridge Prep C18 column (5 μm, 10×150 mm, Waters Corp., USA), and a size of the aptamer was determined through mass spectrometry (MS).

Cotinine-AS1411 and cotinine-CR026 synthesized in the above were dissolved in distilled water, while cotinine-pegaptanib was dissolved in distilled water treated with diethyl pyrocarbonate, since cotinine-pegaptanib is RNA. Then, the resultants were left at 95° C. for 5 minutes and then slowly cooled at a room temperature for 30 minutes followed by storing at −20° C. The structures of cotinine-AS1411 and cotinine-pegaptanib thus obtained were shown in FIG. 3.

(3-3) Conjugate of Cotinine and Abciximab

A conjugate of cotinine and abciximab (cotinine-abciximab) was prepared using abciximab (Reopro).

The conjugate of cotinine and abciximab was prepared by an active ester method. 0.1 mmol of cotinine was added to 1 mL of DMF, and dissolved at a room temperature, and subsequently, a trace of DMAP, 0.118 mmol of DCC and 0.12 mmol of NHS were added thereto and rotated for about 4 hours at a room temperature. The resultant mixture was centrifuged at 10,000×g for 30 minutes to separate supernatant only. 20 mg of abciximab was dissolved in 2 mL of a carbonate buffer, and then 1 mL of DMF was added thereto. The supernatant was slowly put into the mixture and rotated for about 3 hours at a room temperature. Then, the resultant mixture was subjected to a dialysis at least 6 hours at 4° C. and recentrifuged to obtain supernatant only thereby preparing the conjugate.

(3-4) Conjugate of Cotinine and Insulin

A conjugate of cotinine and insulin (cotinine-insulin) was prepared using insulin (SEQ ID NO: 6).

The conjugate of cotinine and insulin was prepared by performing the same method as the method in Example 3-3 for preparing the conjugate of cotinine and abciximab.

Example 4: Preparation of Complex Comprising Conjugate of Cotinine and Binding Material and Anti-Cotinine Antibody To prepare a cotinine-WKYMVm-NH$_2$/anti-cotinine IgG complex, as a complex comprising the conjugate of cotinine and a binding material prepared in Example 1 and the anti-cotinine antibody prepared in Example 2, following processes were performed.

Experimental Example 1: Affinity Analysis of Anti-Cotinine Rabbit/Human Chimeric IgG to Cotinine An affinity of an anti-cotinine rabbit/human chimeric IgG to cotinine is analyzed through surface plasmon resonance (SPR) using BIAcore 3,000 (BIAcore AB, Uppsala, Sweden).

Specifically, cotinine-OVA (ovalbumin) was immobilized to a carboxymethyldextran (CM5)-modified sensor chip (Biacore AB) according to the manual enclosed in a kit with an amine coupling kit (Biacore AB) while flowing 10 mM of sodium acetate buffer (pH 4.0) at a rate of 5 μL/min. The anti-cotinine rabbit/human chimeric IgG antibody dissolved in PBS (pH 7.4) including 0.005% of Tween 20 (sigma, USA), was injected into a chip at a rate of 30 μL/min at 25° C. The anti-cotinine rabbit/human chimeric IgG antibody was diluted to a concentration of 0.15625-10 nM.

Surface was recovered with 1M NaCl/50 mM NaOH, and association dissociation rate constant (kon and koff) and equilibrium dissociation constant (Kd) were obtained by analysis software (BIA evaluation software). The result was shown in table 1 and illustrated as a graph in FIG. 4.

Figure 4:
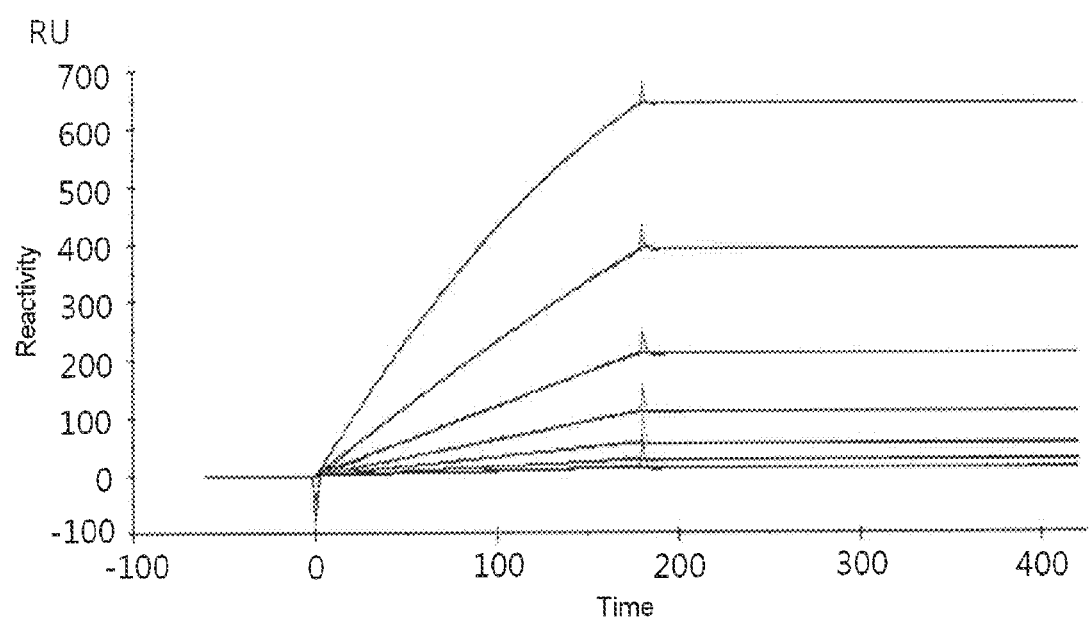
FIG. 4 is an analysis graph showing affinity of an anti-cotinine IgG antibody to cotinine performed in Experimental Example 1.

As shown in FIG. 4, as an amount of the anti-cotinine rabbit/human chimeric IgG antibody injected was increased, an amount of the anti-cotinine IgG antibody, which binds to cotinine immobilized to CMS chip, was increased.

TABLE 1

| Clone | Kon (M$^{-1}$s$^{-1}$) | Koff (M$^{-1}$s$^{-1}$) | KD (M) |
|---|---|---|---|
| anti-cotinine rabbit/human chimeric IgG antibody | 2.559 × 10$^6$ | 1.253 × 10$^{-5}$ | 4.896 × 10$^{-12}$ |

Experimental Example 2: Reactivity Test of Cotinine-WKYMVm-NH$_2$/Anti-Cotinine IgG Complex to Cell Receptor To determine whether a cotinine-WKYMVm-NH$_2$/anti-cotinine IgG complex binds to FPR2, a cell receptor of WKYMVm-NH$_2$, or not, flow cytometry analysis was performed.

A RBL-2H3 cell (Yoe-Sik Bae et al., *J. Immunol.* 2004; 173; 607-614) transfected with FPR2 or a vector (pcDNA3.1) was cultured in RPMI medium supplemented with 10% of fetal bovine serum (FBS) in a condition of 37° C. and 5% CO$_2$. Then, 1×10$^5$ cells were dispensed per each well of a 96-well plate, and subsequently washed twice with PBS and an assay buffer (including 0.02% of azide sodium in 1% of FBS and PBS) for once.

50 μL of the cotinine-WKYMVm-NH$_2$/anti-cotinine IgG complex diluted in the assay buffer was added to each well of RBL-2H3 cells transfected with FPR2, and then the resultant mixture was allowed to react at 4° C. for 30 minutes. In this case, cotinine-WKYMVm-NH$_2$ was tested for 4 different concentrations, i.e., 0, 1, 10 and 100 nM, and a concentration of an anti-cotinine IgG was fixed at 100 nM.

For comparison, the same test was repeated for a RBL-2H3 cell transfected with the vector by using the cotinine-WKYMVm-NH$_2$/anti-cotinine IgG complex.

As an another comparison group, experimental groups 1 and 2 were used, wherein the experimental group 1 is treated with a cotinine-WKYMVm-NH$_2$/non-specific IgG (Palivizumab; Synagis®; Abbot Laboratories, UK) in the same concentration as above to RBL-2H3 cells transfected with FPR2, and the experimental group 2 is treated with wkymvm-NH$_2$ as a negative peptide for WKYMVm-NH$_2$ i.e., 100 nM of a cotinine-wkymvm-NH$_2$/100 nM anti-cotinine antibody Cells were washed twice with the assay buffer then reacted with a FITC labeled monoclonal anti-human Fc specific IgG (Thermo Fisher Scientific, USA), which was diluted in the assay buffer at a ratio of 1:100, added to each well in an amount of 50 μL, followed by a reaction at 4° C. for 20 minutes. Subsequently, cells were washed twice with the assay buffer, and resuspended with PBS and then fixed with 2% of paraformaldehyde (1:1 (v/v)). The fixed cells were measured by using a FACSCanto™ II flow cytometer (BD Bioscience, Germany) and data was analyzed using FlowJo data analysis software (Treestar, USA). The result was shown in FIG. 5.

As shown in FIG. 5, it could be understood that the cotinine-WKYMVm-NH$_2$/anti-cotinine IgG complex was specifically bound to the RBL-2H3 cell transfected with FPR2, and the binding ability was increased as the concentration of cotinine-WKYMVM-NH$_2$ was increased.

In contrast, it was determined that the complex did not bind to the RBL-2H3 cell transfected with the vector. Also, it was determined that the cotinine-WKYMVm-NH$_2$/non-specific IgG complex and the cotinine-wkymvm-NH$_2$/anti-cotinine IgG complex did not bind to the RBL-2H3 cell transfected with FPR2.

Experimental Example 3: Measuring Whether Functional Activity of Cotinine-WKYMVm-NH$_2$/Antibody Complex to WKYMVM-NH$_2$ Peptide was Maintained or Not (In Vitro Assay)

(3-1) Change in Calcium Concentration in Cell

A calcium concentration in a cell ([Ca$^{2+}$]i) was measured by Grynkiewicz method using Fura-2/AM (see publication [Grynkiewicz G. et al., *J Biol. Chem.*, 260, p 3440-3450 1985]).

A neutrophil was freshly separated from human peripheral blood by using dextran sedimentation, hypotonic lysis of erythrocytes, and lymphocyte separation medium gradient. Then, 3 μM of Fura-2/AM diluted in 4 mL of fresh serum-free RPMI 1640, was added to the separated neutrophil, and then the resultant mixture was cultured at 37° C. for 50 minutes with constant stirring. After washing three times with serum-free RPMI 1640, 2×10$^6$ cells were dispensed to 1 mL of Ca$^{2+}$-free Locke solution (154 mM NaCl, 5.6 mM KCl, 1.2 mM MgCl$_2$, 5 mM HEPES [pH 7.3], 10 mM glucose, and 0.2 mM EGTA). WKYMVm-NH$_2$ (1, 2.5, 5, 10 and 100 nM), cotinine-WKYMVm-NH$_2$ (1, 2.5, 5, 10 and 100 nM), a cotinine-WKYMVm-NH$_2$ (1, 2.5, 5, 10 and 100 nM)/anti-cotinine IgG complex (mole concentration 2:1) were respectively added to the dispensed cells.

Experimental groups treated with wkymvm-NH$_2$ (100 nM), which is a non-specific peptide, cotinine-wkymvm-NH$_2$ (100 nM), cotinine-wkymvm-NH$_2$ (100 nM)/50 nM anti-cotinine IgG, respectively, were used as comparison groups.

A fluorescence value at 500 nm for two excitation wavelengths at 340 nm and 380 nm was measured using RF-5301PC spectrofluorophotometer (Shimadzu Instruments Inc., Japan). The result was shown in FIG. 6. An increase in a calcium concentration in the cell leads to an increase in a ratio of fluorescence value of excitation efficiency at 340 nm to excitation efficiency at 380 nm.

Figure 6:
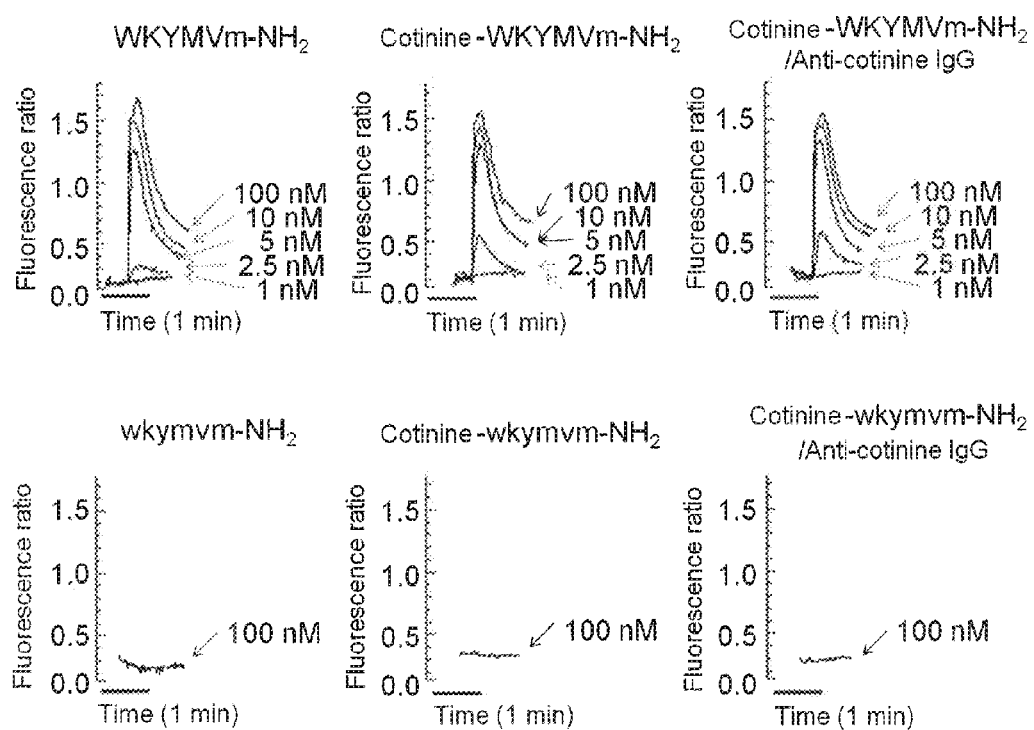
FIGS. 6 to 8 show analysis results of a change in intracellular calcium concentration, a production degree of superoxide, and chemotaxis, of the cotinine-WKYMVm-NH$_2$/anti-cotinine IgG complex, respectively.

As shown in FIG. 6, concentration-dependencies of WKYMVm-NH$_2$, cotinine-WKYMVm-NH$_2$ and the cotinine-WKYMVm-NH$_2$/anti-cotinine IgG complex were similar. Also, cotinine-WKYMVm-NH$_2$ and the cotinine-WKYMVm-NH$_2$/anti-cotinine IgG complex strongly induced an increase in a calcium concentration in a cell, as WKYMVm-NH$_2$ did. In contrast, any specific increase in calcium was not showed in the cases of wkymvm-NH$_2$, cotinine-wkymvm-NH$_2$ and the cotinine-wkymvm-NH$_2$/anti-cotinine IgG complex.

(3-2) Superoxide Generation

Generation of a superoxide may be measured by measuring a reducing value of cytochrome c dependent on superoxide (see publication [Bae et al., *Blood*, 97, p 2854-2862, 2001]).

Specifically, human neutrophils dispensed in RPMI 1640 medium in a number of 2×10$^6$ were pre-cultured for 1 minute at 37° C. with 50 μM of cytochrome c, then reacted with WKYMVm-NH$_2$ (0, 10, 100 and 1,000 nM), cotinine-WKYMVm-NH$_2$ (0, 10, 100 and 1,000 nM), and cotinine-WKYMVm-NH$_2$ (0, 10, 100 and 1,000 nM)/anti-cotinine IgG (mole ratio 2:1), respectively.

Experimental groups treated with wkymvm-NH$_2$ (0, 10, 100 and 1,000 nM), and cotinine-wkymvm-NH$_2$ (0, 10, 100 and 1,000 nM)/anti-cotinine IgG (mole ratio 2:1), respectively, were used as comparison groups.

A change in absorbance at 550 nm, depending on reducing of cytochrome c, was measured for 5 minutes at intervals of one minute using a spectrophotometer (EL312e; Bio-Tek instruments, Winooski, Vt.). The value was shown in nanomole unit by dividing an absorbance value, obtained by subtracting an absorbance value at 0 minute from a measured value of absorbance thereafter, by 0.022 μM$^{-1}$ cm$^{-1}$, which is an extinction coefficient. The result was shown in FIG. 7.

Figure 7:
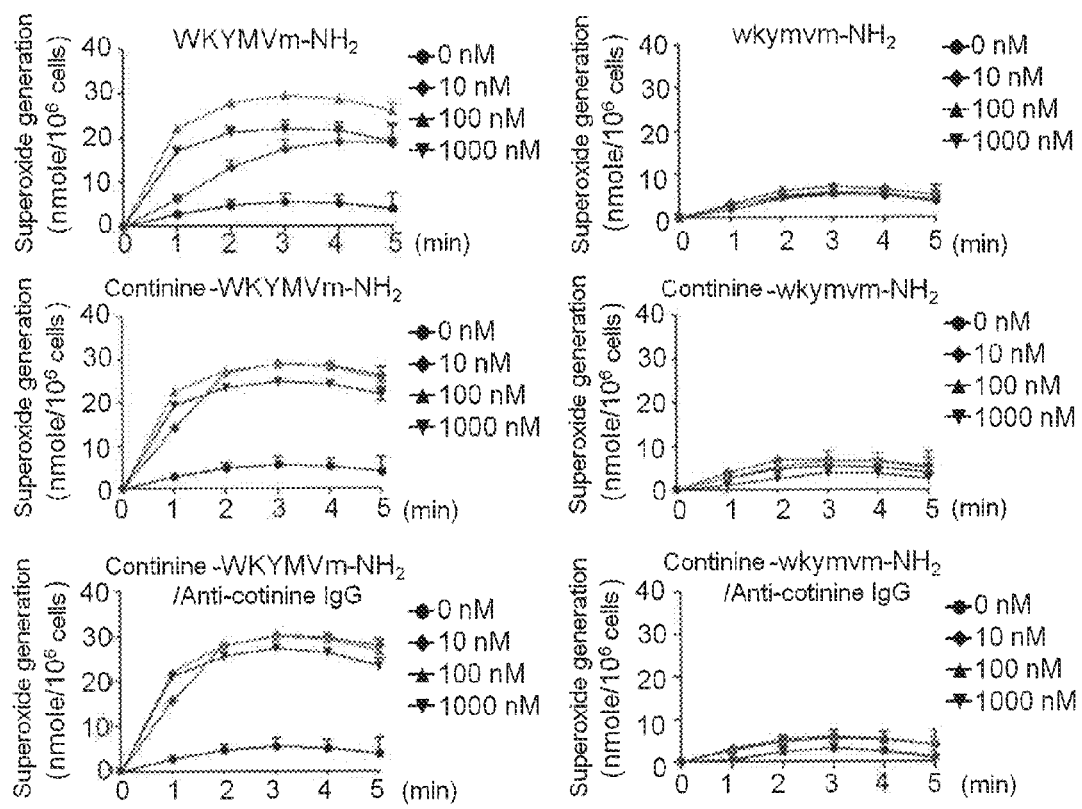

As shown in FIG. 7, concentration-dependencies of WKYMVm-NH$_2$, cotinine-WKYMVm-NH$_2$, and the cotinine-WKYMVm-NH$_2$/anti-cotinine IgG complex were similar, and it was determined that cotinine-WKYMVm-NH$_2$ and the cotinine-WKYMVm-NH$_2$/anti-cotinine IgG complex strongly induced superoxide generation, as WKYMVm-NH$_2$ did. In contrast, any specific a superoxide generation was not showed in the cases of wkymvm-NH$_2$, a cotinine-wkymvm-NH$_2$ conjugate and the cotinine-wkymvm-NH$_2$/anti-cotinine IgG complex.

(3-3) Chemotaxis Analysis

Human neutrophils were dispensed to RPMI 1640 medium in a number of 1×10$^6$/mL, and 25 μl of the cell suspension solution was added in an upper well of a Mutiwell chamber (Neuroprobe, USA) (see publication [Bae et al., *Blood*, 97, p 2854-2862, 2001]). The upper well of the Multiwell chamber was separated from a bottom well, having WKYMVm-NH$_2$ (0, 10 or 100 nM), cotinine-WKYMVm-NH$_2$ (0, 10 or 100 nM) and cotinine-WKYMVm-NH$_2$ (0, or 100 nM)/anti-cotinine IgG (mole ratio 2:1), by a 3 μm of polyhydrocarbon filter.

Experimental groups treated with wkymvm-NH$_2$ (0, 10, and 100 nM), cotinine-wkymvm-NH$_2$ (0, 10, and 100 nM) and cotinine-wkymvm-NH$_2$ (0, 10, and 100 nM)/anti-cotinine IgG (mole ratio 2:1), respectively, were used as comparison groups.

The samples were maintained at 37° C. for 90 minutes, then cells which did not migrate were removed by scraping, and the migrated cells passed through the filter were fixed overnight by adding 4% of paraformaldehyde. The fixed filter was treated with 90%, 80%, and 70% ethanol and deionizing water sequentially, followed by drying in the air. The dried filter was stained using haematoxylin (Sigma-Aldrich, USA). The stained cells in each well was counted five times after randomly selected in high-power fields (400×). The result was shown in FIG. 8.

Figure 8:
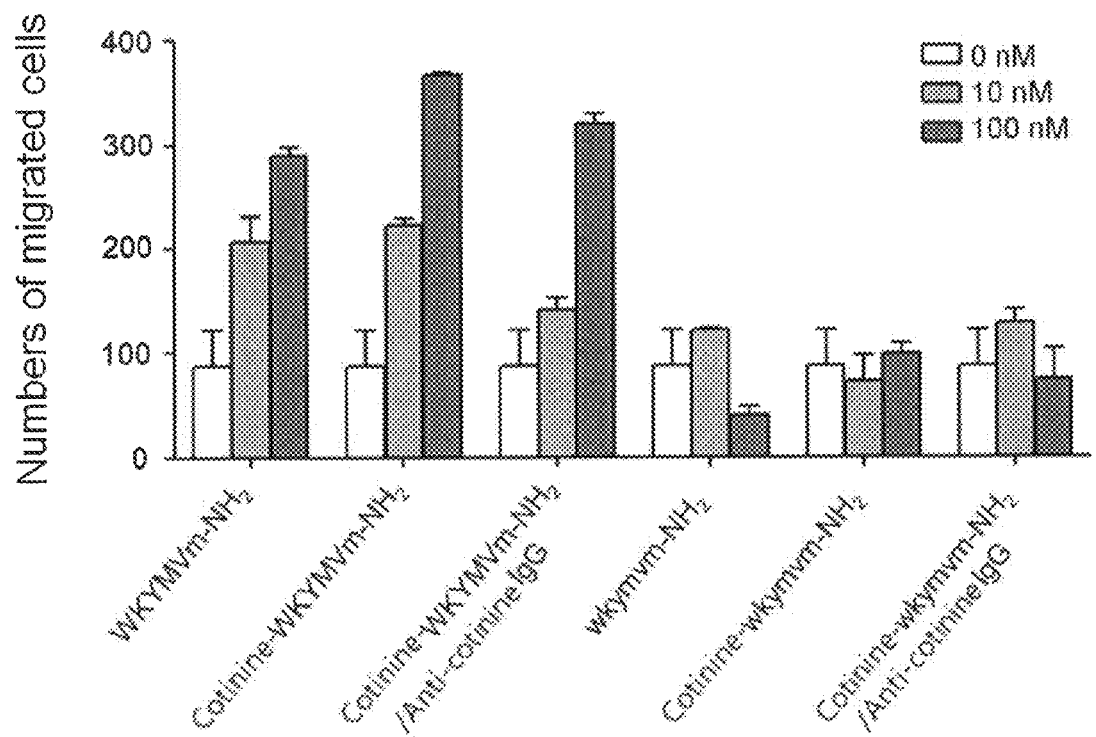

As shown in FIG. 8, concentration-dependencies of WKYMVm-NH$_2$, cotinine-WKYMVm-NH$_2$ and the cotinine-WKYMVm-NH$_2$/anti-cotinine IgG complex were similar, and they strongly facilitated migration of neutrophiles. In contrast, no specific migration of cells was shown in the cases of wkymvm-NH$_2$, the cotinine-wkymvm-NH$_2$ conjugate and the cotinine-wkymvm-NH$_2$/anti-cotinine IgG complex.

Experimental Example 4: Pharmacokinetics of Cotinine-WKYMVm-NH$_2$ and Cotinine-WKYMVm-NH$_2$/Anti-Cotinine IgG Complex Male wild-type albino ICR mice aged 4 to 6 weeks (Institute of Cancer Research Center, ORIENT BIO Inc., Korea) were injected through tail vein with cotinine-WKYMVm-NH$_2$ (0.5 mg/kg) and a cotinine-WKYMVm-NH$_2$ (0.5 mg/kg)/anti-cotinine IgG (10 mg/kg) complex diluted in 100 μL of PBS, respectively.

In the case of a mouse injected with cotinine-WKYMVm-NH$_2$, peripheral blood was obtained at 0, 0.5, 1, 2, 3, 4, 5, 6, 8, 10, 12, 16, 20 and 24 hours after the injection through the orbital plexus, and in the case of a mouse injected with the cotinine-WKYMVm-NH$_2$/anti-cotinine IgG complex, peripheral blood was obtained at 0, 0.5, 1, 2, 3, 4, 5, 6, 8, 10, 12, 16, 20, 24, 48, 72, 96, 120, 144 and 168 hours after the injection through the orbital plexus. Each peripheral blood was maintained at a room temperature for 30 minutes, and then centrifuged at 800 g for 15 minutes. Then, serum was obtained by collecting supernatant only and each serum was analyzed by flow cytometry analysis.

Each serum was diluted in an assay buffer (1% FBS, and 0.02% azide sodium (NaN$_3$) in PBS) and then 200 nM of anti-cotinine IgG was added in the same amount and measured after cotinine-WKYMVm-NH$_2$ in serum completely form a complex with the anti-cotinine IgG.

1×10$^5$ RBL-2H3 cells transfected with FPR2 were reacted with the mixture at 4° C. for 30 minutes. Then, the cells were washed twice with the assay buffer and reacted with a FITC labeled monoclonal anti-human Fc specific IgG (Thermo Fisher Scientific, USA), which was diluted in the assay buffer at a ratio of 1:100, added to each well, at 4° C. for 20 minutes.

The resulting cells were washed twice with the assay buffer and added with a FITC labeled monoclonal anti-human Fc specific IgG (Thermo Fisher Scientific, USA) diluted in the assay buffer at a ratio of 1:100 to each well in an amount of 50 μL, at 4° C., and allowed to react for 20 minutes. The resulting cells were washed twice with the assay buffer, and resuspended in PBS and then fixed through 2% of paraformaldehyde (1:1 (v/v)). The fixed cells were measured by using FACSCanto™ II flow cytometer (BD Bioscience, Germany) and data was analyzed using FlowJo data analysis software (Treestar, USA). The result was shown in FIG. 9.

Figure 9:
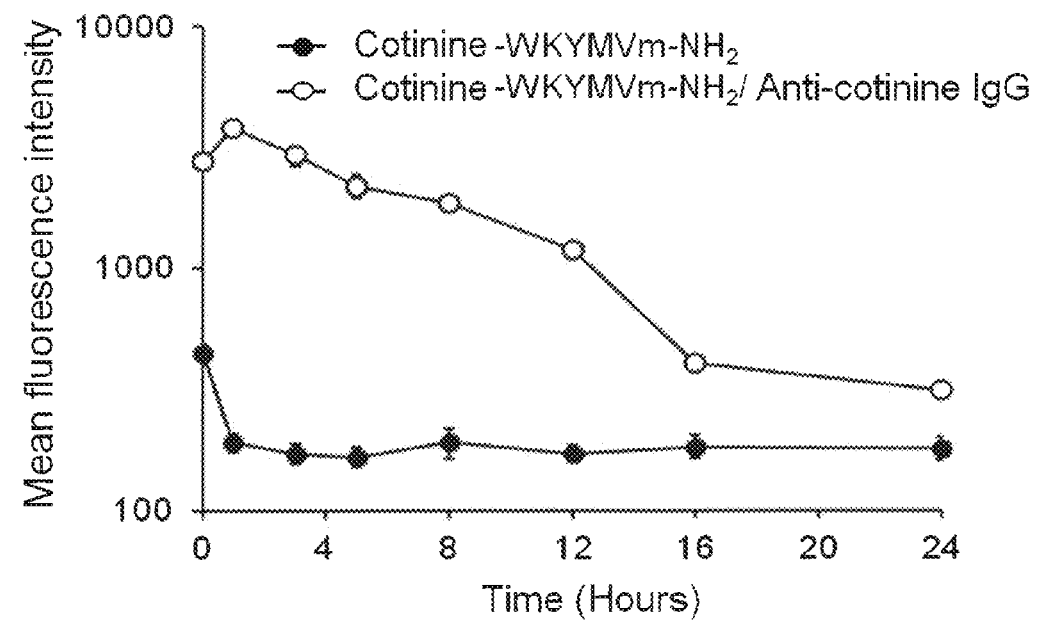
FIG. 9 shows a graph and a histogram comparing the in vivo half-life of the cotinine-WKYMVm-NH$_2$ conjugate to that of the cotinin-WKYMVm-NH$_2$/anti-cotinine IgG complex in mice.
Figure 9:
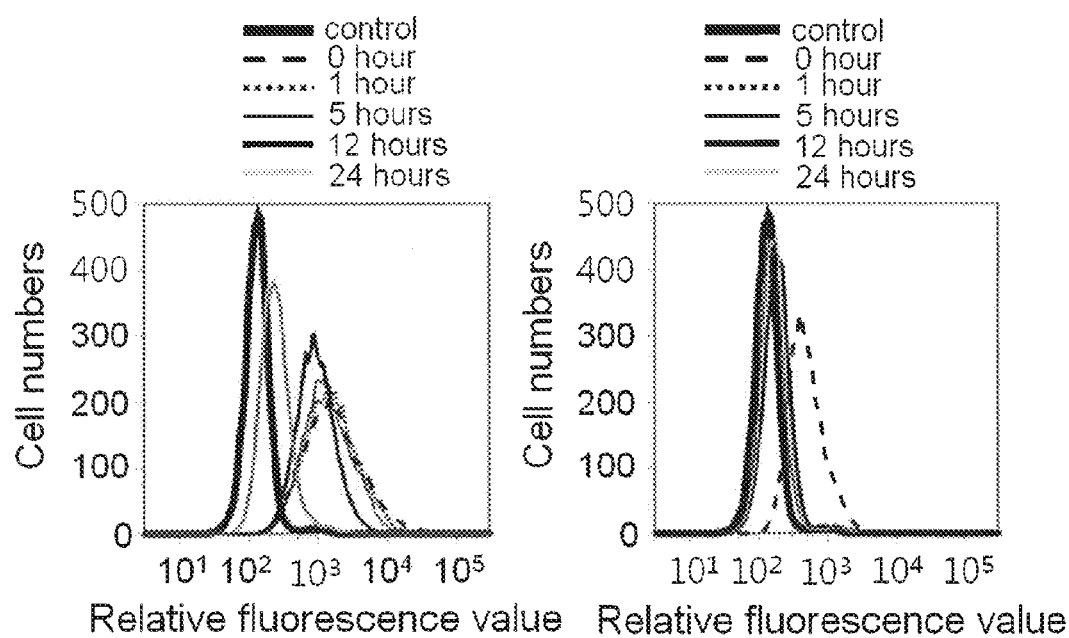

As shown in FIG. 9, comparing mean fluorescence intensity values, those of a serum from a mouse injected with the cotinine-WKYMVm-NH$_2$/anti-cotinine IgG complex was maintained higher than half of the peak for about 8 hours and higher than background for 16 hours. In contrast, those of a serum from a mouse injected with cotinine-WKYMVm-NH$_2$ was become lower than background after one hour.

Experimental Example 5: Pharmacokinetics of Anti-Cotinine IgG

Male wild-type albino ICR mouse (ORIENT BIO Inc., Korea) aged from 4 to 6 weeks were injected through tail vein with an anti-cotinine IgG (10 mg/kg) diluted in 100 μL of PBS, and then peripheral blood was obtained through the orbital plexus at 0, 1, 3, 6, 12 hours and 1, 2, 3, 4, 5, 6, 7, 10, 14, 21, 28 days after the injection. Each peripheral blood was maintained at a room temperature for 30 minutes, and centrifuged at 800 g for 15 minutes to collect supernatant only so that serum was obtained. Then, ELISA was performed to measure an amount of the anti-cotinine IgG in serum.

Each well of a 96-well ELISA plate was coated with 5 μg/mL of cotinine-BSA diluted in PBS overnight, and then blocked by PBSB (3% BSA in PBS). The serum thus obtained was diluted in PBSB (1:10 to 1:1,000), and added to each coated well in an amount of 50 μL. Subsequently, it was maintained at a room temperature for one hour and then washed with PBS-T (0.02% Tween 20 in PBS). HRP-bound sheep anti-human Fc specific IgG (Thermo Fisher Scientific) was added to each well and the mixture was maintained for 30 minutes at a room temperature, and then the optical density was measured at 405 nm using ABST (one-step ABTS solution, Sigma) as a substrate. The result was shown in FIG. 10.

Figure 10:
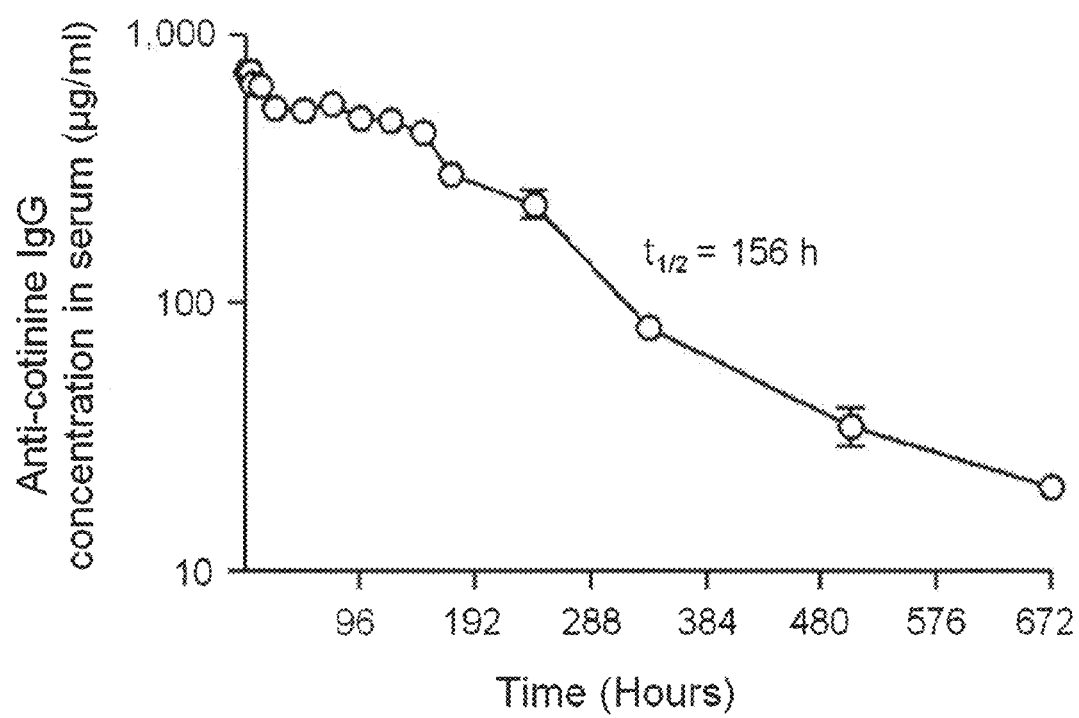
FIG. 10 is a graph showing the in vivo half-life of the anti-cotinine IgG in serum.

As shown in FIG. 10, it can be determined that a half-life of the anti-cotinine IgG in serum is more than six days.

Experimental Example 6: Therapeutic Effect of Cotinine-WKYMVm-NH$_2$/Anti-Cotinine IgG Complex in a Mouse Septicemia Model Cecum was separated from an ICR mouse through 2 cm incision of abdominal wall of the mouse. 25% of the obtained cecum was ligated at subjacent of ileocecal valve, and then the cecum was penetrated with a 22 gauge needle and treated so that stool went into abdominal cavity. The muscle of abdominal wall and the dermal layer were sutured. In an experimental group of a sham-operated mouse, the cecum was separated through 2 cm incision of abdominal wall of the mouse, and then the cecum was put into abdominal cavity again without any treatment. Mice received CLP were divided into 6 groups (20 animals per each group), and injected via tail vein with cotinine-WKYMVm-NH$_2$ (0.4 mg/kg and 0.04 mg/kg)/anti-cotinine IgG (18 mg/kg and 1.8 mg/kg) complex experimental group, cotinine-WKYMVm-NH$_2$ (0.4 mg/kg) experimental group, WKYMVm-NH$_2$ only (0.2 mg/kg) experimental group, anti-cotinine IgG only (18 mg/kg) experimental group and PBS vehicle control group (all injected with 100 μL) for two days at intervals of 12 hours started from two hours after CLP.

The treated mice were observed for ten days after put into a breeding facility while providing water and feed. Subsequently, the survival rate of the mice was analyzed and the result was shown in FIG. 11.

Figure 11:
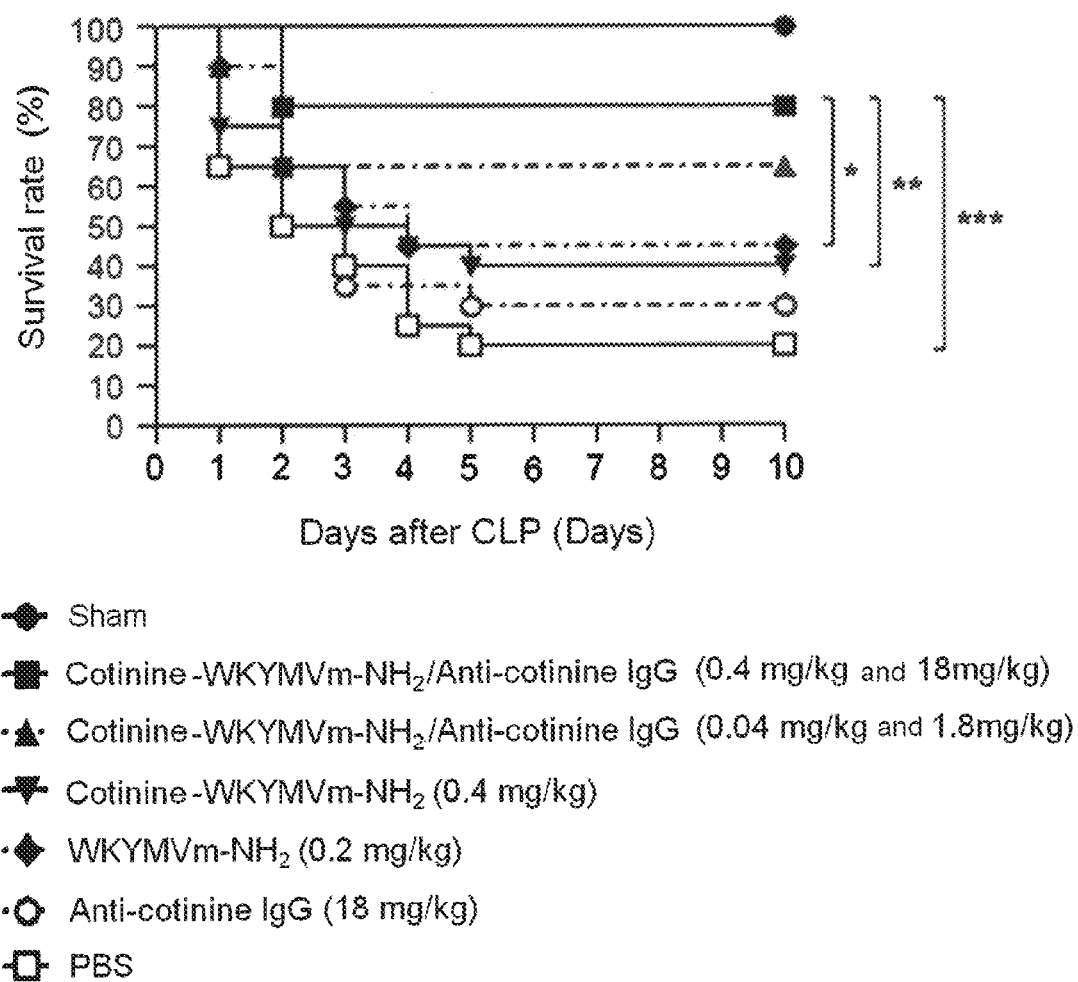
FIG. 11 is a graph showing improved therapeutic efficiency of the cotinine-WKYMVm-NH$_2$/anti-cotinine IgG complex in a sepsis model.

As shown in FIG. 11, the experimental group injected with the cotinine-WKYMVm-$NH_2$/anti-cotinine IgG complex exhibits approximately 80% of survival rate. It can be understood that the survival rate of the cotinine-WKYMVm-$NH_2$/anti-cotinine IgG complex experimental group was relatively improved compared with those of cotinine-WKYMVm-$NH_2$ experimental group (40%), WKYMVm-$NH_2$ experimental group (45%), and PBS vehicle control group (20%).

Experimental Example 7: Pharmacokinetics of Cotinine-Pegaptanib and Cotinine-Pegaptanib/Anti-Cotinine IgG Complex Male wild-type ICR mouse aged from 4 to 6 weeks were injected through tail vein with cotinine-pegaptanib (0.135 mg/kg) and a cotinine-pegaptanib (0.135 mg/kg)/anti-cotinine IgG (1 mg/kg) complex, diluted in 100 μL of PBS. Each peripheral blood was obtained through the orbital plexus at 0, 0.5, 1, 1.5 and 2 hours after the injection, and the obtained peripheral blood was maintained at a room temperature for 30 minutes then centrifuged at 800 g for 15 minutes to collect supernatant only so that serum was obtained, and analyzed by using ELISA.

Each well of a 96-well ELISA plate was coated with 50 ng of human VEGF dissolved in PBS overnight, and then blocked by PBSB. Then, each serum was diluted in PBSB at a ratio of 1:100, and added to each well with 100 nM of an anti-cotinine IgG The plate was maintained at a room temperature for one hour and washed with PBS-T, and then HRP-bound rabbit anti-human Fc specific IgG (Thermo Fisher Scientific) was added to each well. The resultant mixture was maintained at room temperature for one hour. Subsequently, 3,3',5,5'-tetramethylbenzidine (TMB) (Thermo Fisher Scientific) was added as a substrate to the resultant mixture, and kept at a room temperature for 15 minutes, followed by measuring the optical density at 650 nm. The result was shown in FIG. 12.

Figure 12:
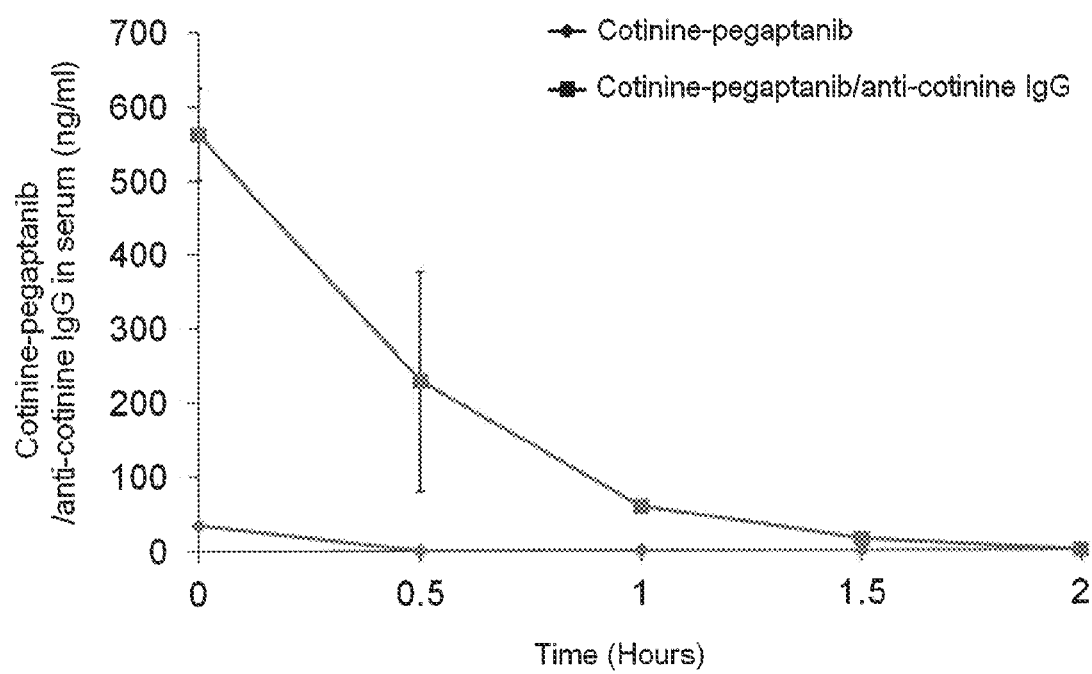
FIG. 12 is a graph comparing the in vivo half-life of the cotinine-pegaptanib conjugate to that of a cotinine-pegaptanib/anti-cotinine IgG complex in mice.

As shown in FIG. 12, it can be understood that the half-life of cotinine-pegaptanib/anti-cotinine IgG complex in serum was considerably increased comparing with those of cotinine-pegaptanib. Also, it showed that the concentration at 0 hour of the complex was higher, which suggests a rapid degradation of cotinine-pegaptanib was inhibited in the case of injecting the cotinine-pegaptanib/anti-cotinine IgG complex, while cotinine-pegaptanib was degraded immediate after injection into the body.

Experimental Example 8: Biological Analysis of Cotinine-Aptamer/Anti-Cotinine IgG (8-1) Binding of Cotinine-AS1411/Anti-Cotinine IgG Complex to Nucleolin of Cell Surface of Cotinine-Aptamer/Anti-Cotinine IgG Raji cells (human Burkitt's lymphoma, American Type Culture Collection, USA) were dispensed in 1×10⁵ cells per each well, and treated with a cotinine-AS1411 (1, 10, 50 and 100 nM)/anti-cotinine IgG (100 nM) complex in an amount of 50 μL/sample, followed by allowing to react at 4° C. for 20 minutes. Then, cells were washed with an assay buffer (1% FBS, and 0.02% azide sodium ($NaN_3$) in PBS) twice and added with a FITC labeled monoclonal anti-human Fc specific IgG (Thermo Fisher Scientific, USA), which was diluted in the assay buffer at a ratio of 1:100 to each well, at 4° C., and allowed to react for 15 minutes.

The same method was performed using a cotinine-CR026/anti-cotinine IgG complex, which was prepared by using a non-specific aptamer CR026 (ST Pharm, Korea), and a cotinine-AS1411/Palivizumab (Abbot Laboratories, Kent, UK) complex, which was prepared by using Palivizumab, a non-specific control antibody, as comparison groups.

Also, as a background control, the cells were allowed to react with FITC labeled monoclonal anti-human Fc specific IgG (Thermo Fisher Scientific) only, and subsequent reactions were performed in the same manner as described above.

The cells obtained in above were washed twice with the assay buffer, and resuspended with PBS, and then fixed with 2% of paraformaldehyde (1:1 (v/v)). Then, the cells were subjected to FACSCanto™ II flow cytometer (BD Bioscience, Germany), and data was analyzed using FlowJo data analysis software (Treestar, USA). The results were shown in FIGS. 13 and 14.

Figure 13:
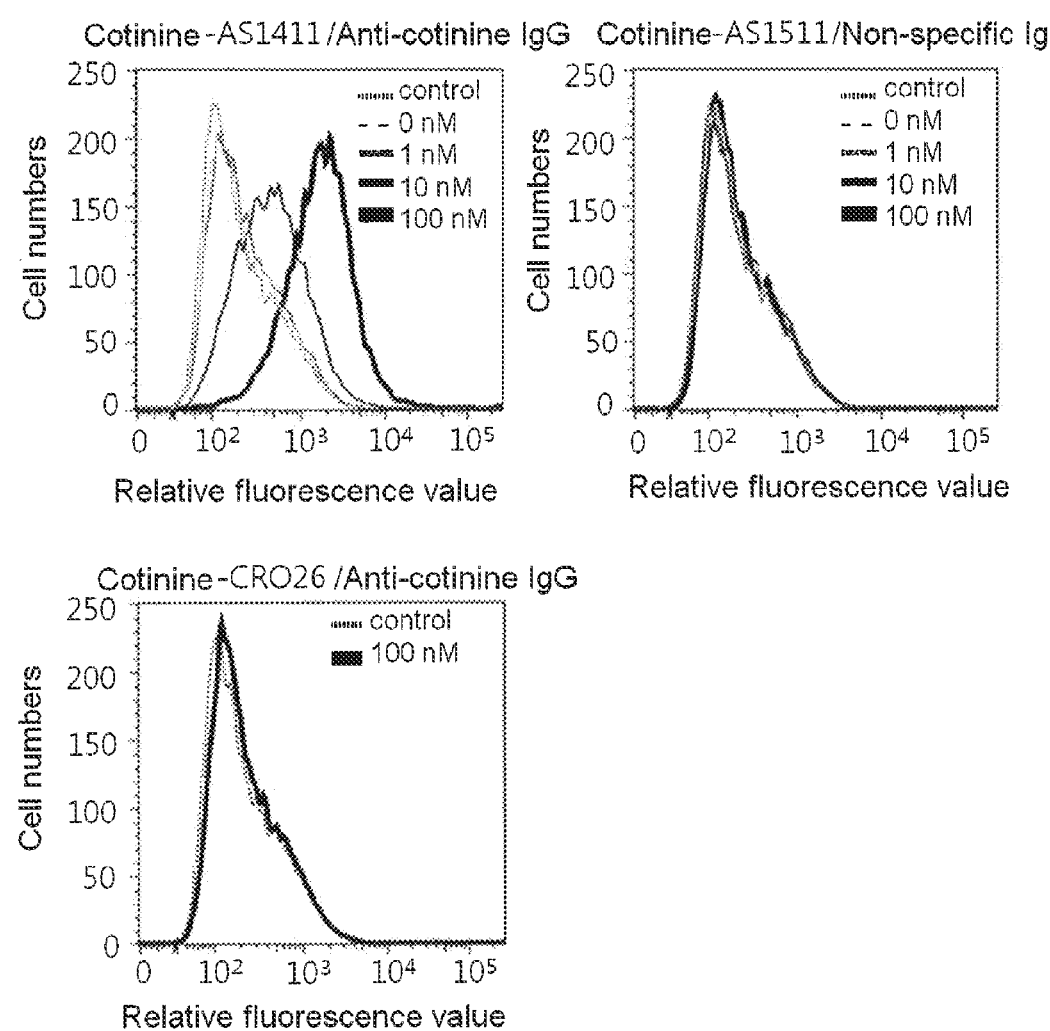
FIGS. 13 and 14 show test results of a specific binding ability of a cotinine-AS1411/anti-cotinine IgG complex to a nucleolin cell receptor.

As shown in FIG. 13, the binding ability of the cotinine-AS1411/anti-cotinine IgG complex to nucleolin on a surface of a cell was increased as a concentration of cotinine-AS1411 was increased. In contrast, in the case of a complex including a non-specific aptamer (CR026) or a non-specific antibody (palivizumab), binding ability to nucleolin was not observed.

Figure 14:
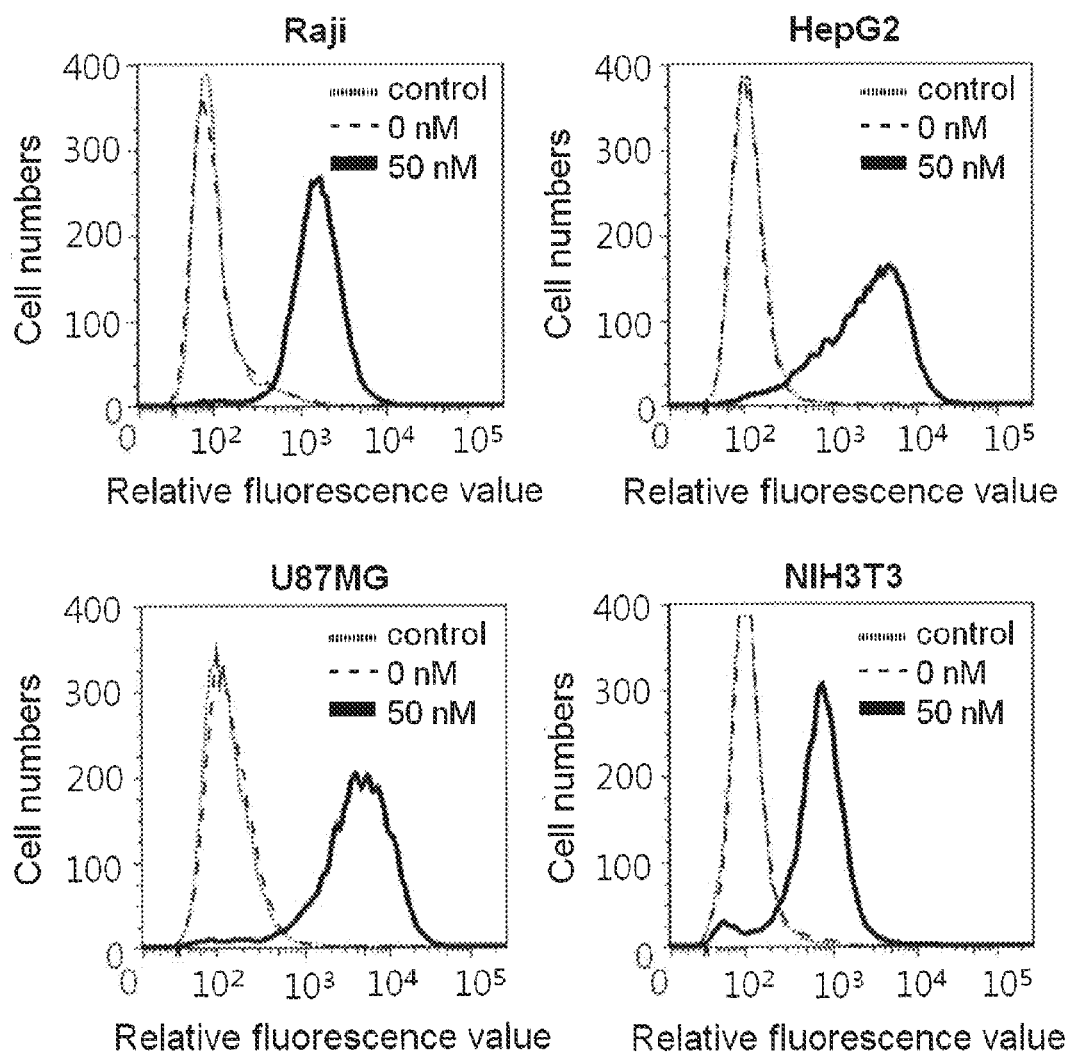

Also, as shown in FIG. 14, the cotinine-AS1411 (50 nM)/anti-cotinine IgG (100 nM) complex was treated with human hepatocellular carcinoma (HepG2), human glioblastoma (U87MG), and mouse embryonic fibroblast (NIH3T3) (American Type Culture Collection, USA) so that the difference between an expression level of nucleolin among cells was determined. As a result, it can be understood that HepG2 cells and U87MG cells exhibited stronger binding ability, while NIH3T3 cells exhibited weaker binding ability as compared to Raji cells.

(8-2) Western-Blot Using Cotinine-AS1411/Anti-Cotinine IgG Complex

After washing Raji cells with PBS three times, adding 1 mL of a lysis buffer (20 mM Tris-Cl, pH 7.5, 150 mM NaCl, 1% Triton X-100, 0.25 mM synthetic dextrose complete medium, 1 mL of phenylmethanesulfonyl fluoride (PMSF), 1 μg/mL of aprotinin, 1 μg/mL of leupeptin, and 1 μg/mL of pepstatin A), and subjected to sonication three times for 10 seconds in a condition of output setting 7 using a sonic dismembrator model 500 (Thermo Fisher Scientific). After centrifuging for ten minutes at 17,000×g, only the supernatant was collected and the concentration was measured by Bradford assay (Bio-rad, USA).

50 μg of a lysate was added with 4×SDS loading buffer (50 mM MES, 50 mM Tris-base, 0.1% SDS, 1 mM EDTA, and 50 mM dithiothreitol (pH 7.3)) and boiled at 95° C. for 10 minutes, thereby denaturing a protein, and then SDS-polyacrylamide gel electrophoresis (SDS-PAGE) was performed on 4-12% of Bis-Tris gel (Invitrogen). A protein was transferred to a nitrocellulose membrane (Whatman, Germany) using XCell SureLock™ Novex Mini-Cell (Invitrogen). Then, the resultant was cultured at a room temperature for 30 minutes with shaking in TBST (10 mM Tris, pH 7.5, 150 mM NaCl, and 0.1% Tween-20) containing 5% skim milk (BD Biosciences Diagnostic Systems, USA), and then cultured with the cotinine-AS1411 (100 nM)/anti-cotinine IgG (50 nM) complex for 2 hours at a room temperature with shaking.

For comparison, the procedures of the above experiment was repeated except for using mouse anti-nucleolin IgG (Santa Cruz Biotechnology, USA) diluted in a blocking buffer at a ratio of 1:100.

Also, as comparison groups, the experimental groups treated with a cotinine-AS1411 (100 nM)/non-specific antibody (palivizumab) (50 nM) complex, and a cotinine-CR026 (100 nM)/anti-cotinine IgG (50 nM) complex were used.

The membrane was washed with TBST three times, a HRP bound rabbit anti-human IgG (Theremo Fisher Scientific) and a HRP bound anti-mouse IgG (Thermo Fisher Scientific), which were diluted in TBST at a ratio of 1:5,000, were added, and then the resultant mixture was cultured at a room temperature for one hour with shaking. The membrane was washed three times with TBST, SuperSignal Pico West chemiluminescent substrate (Thermo Fisher Scientific) was added to visualize a protein band. The result was shown in FIG. 15.

Figure 15:
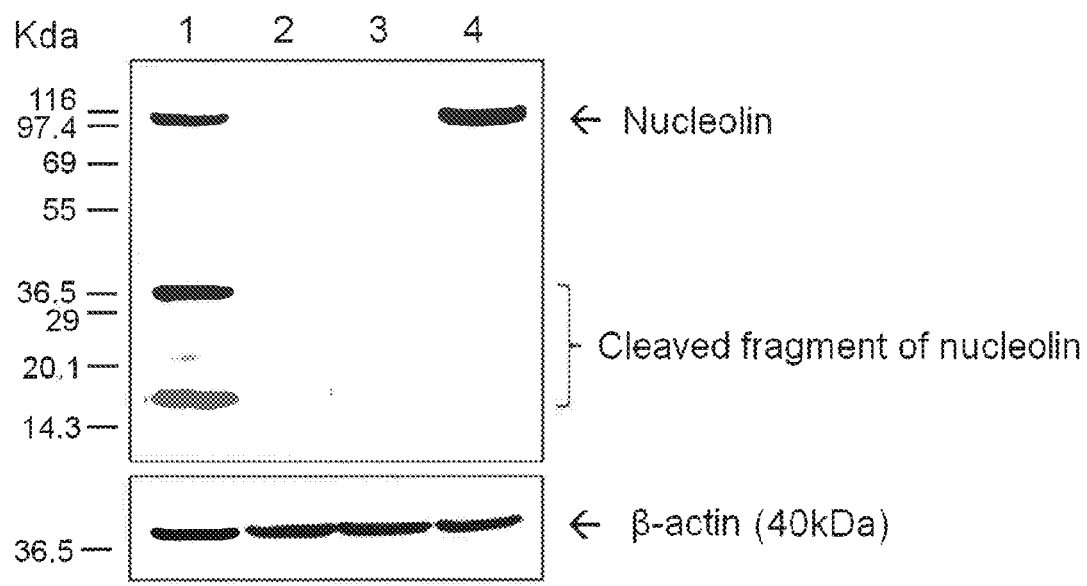
FIG. 15 shows a Western blotting result of the cotinine-AS1411/anti-cotinine IgG complex.

As shown in FIG. 15, the lane 1, which was treated with the cotinine-AS1411/anti-cotinine IgG complex showed several bands no more than 40 kDa, as well as a 100 kDa of full-length nucleolin band. According to the existed report, those were small size fragments which were produced by cutting nucleolin due to the autolytic activity of nucleolin showing that not only a full-length of the cotinine-AS1411/anti-cotinine IgG complex but also small fragments can be detected.

In contrast, in lane 4 of mouse anti-nucleolin IgG, only a full-length nucleolin was detectable. No band was shown in the lane 2 of the cotinine-AS1411 (100 nM)/palivizumab (50 nM) complex and the lane 3 of the cotinine-CR026 (100 nM)/anti-cotinine IgG complex.

(8-3) Determination of Availability of Immunoprecipitation of Nucleolin Using Cotinine-AS1411/Anti-Cotinine IgG Complex 1 mg of a Raji cell lysate were left overnight under constant stirring with a cotinine-AS1411 (40 nM)/anti-cotinine IgG (20 nM) complex, a cotinine-CR026 (40 nM)/anti-cotinine IgG (20 nM) complex, and a cotinine-AS1411 (40 nM)/non-specific antibody (20 nM) complex.

40 µL of a protein A sepharose bead was added to each sample, and then left at 4° C. for two hours with rotation, and the mixture was centrifuged at 800×g for 1 minute. Then, immunoprecipated pellet was washed three times with a washing buffer (20 mM Tris-Cl, pH 7.5, 150 mM NaCl, and 1% Triton X-100). 4×SDS loading buffer was added thereto, and the resulting mixture was boiled at 95° C. for 10 minutes to denature the protein, and subjected to an immunoblot. A mouse anti-nucleolin IgG (Santa Cruze Biotechnology, USA), which was diluted in 0.2% of TBST at a ratio of 1:100, as a first antibody, was added then left for two hours at a room temperature. An HRP-bound rabbit anti-mouse IgG, which was diluted at a ratio of 1:5,000, as a second antibody, was added then left at a room temperature for one hour. A membrane was washed and added with SuperSignal Pico West chemiluminescent substrate to visualize blot. The result was shown in FIG. 16.

Figure 16:
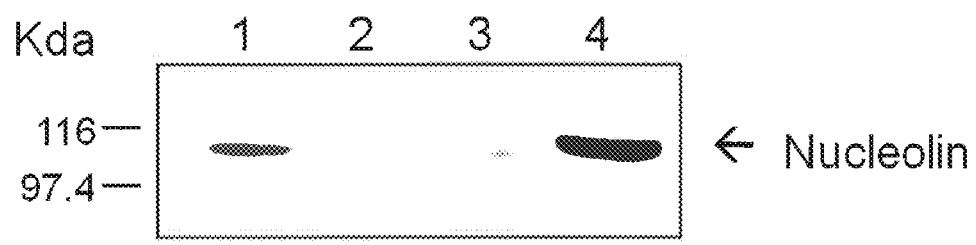
FIG. 16 shows an immunoprecipitation result of nucleolin using the cotinine-AS1411/anti-cotinine IgG complex.

As shown in FIG. 16, in the case of immunoprecipating with the cotinin-AS1411/anti-cotinine IgG complex shown in the lane 1, a 100 kDa of nucleolin band was observed, while in the case of immunoprecipating with the cotinine-CR026/anti-cotinine IgG complex, and the cotinin-AS1411/non-specific antibody complex shown in the lanes 2 and 3 respectively, no band was observed. As can be seen from the above, it can be understood that the cotinine-AS1411/anti-cotinine IgG complex immunoprecipates nucleolin successfully in a lysate of Raji cells.

(8-4) Measuring Specific Binding Ability of Cotinine-Pegaptanib/Anti-Cotinine IgG Complex to VEGF Each well of a 96-well plate was coated with 50 ng of human VEGF, which was dissolved in PBS at 4° C. overnight, and blocked with PBSB. A 100 nM of cotinine-pegaptanib/50 nM anti-cotinine antibody complex, which was diluted in PBSB, was diluted in ten-fold and then added to each coated well in an amount of 50 µL. Subsequently, the plate was left at a room temperature for one hour and then washed with PBS-T. For comparison, the same experiment as above was repeated except for using 100 nM of bevacizumab, as an antibody to VEGF, instead of the complex.

Then, a HRP-bound rabbit anti-human Fc specific IgG (Thermo Fisher Scientific) was added to each well, and the plate was maintained at a room temperature for one hour, followed by measuring the optical density at 650 nm using a TMB (Thermo Fisher Scientific) as a substrate. The result was shown in FIG. 17.

Figure 17:
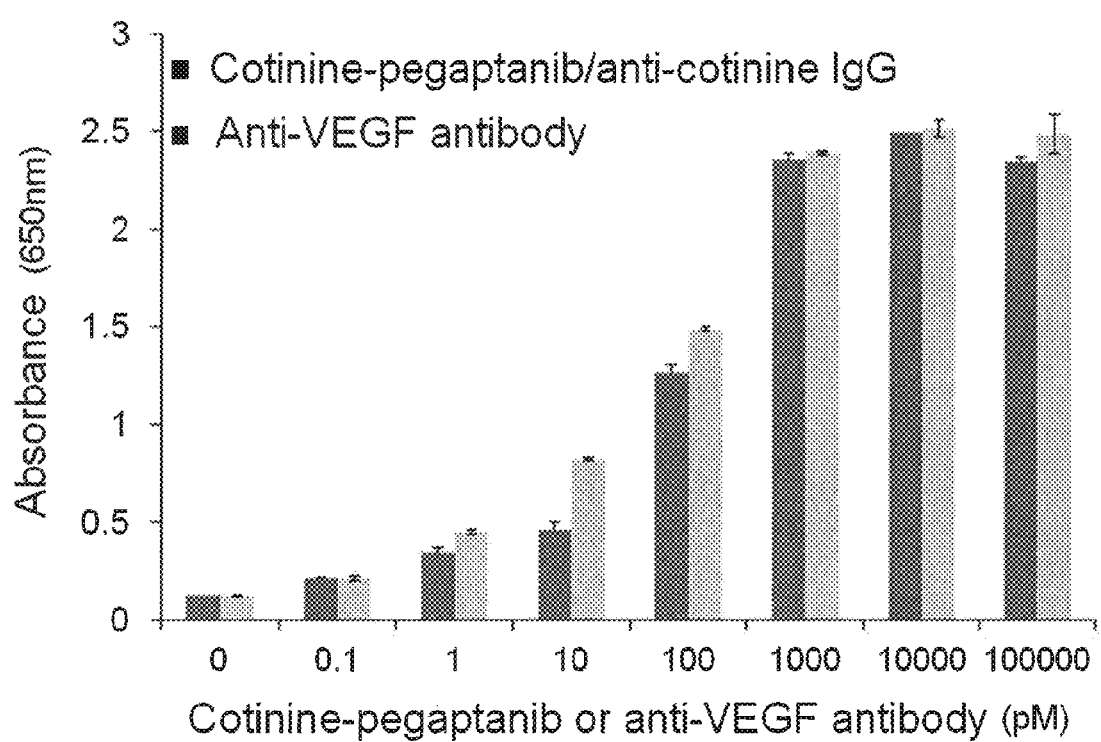
FIG. 17 is a graph showing a binding activity of the cotinine-AS1411/anti-cotinine IgG complex to VEGF.

As shown in FIG. 17, the binding ability of the cotinine-pegaptanib/anti-cotinine IgG complex to VEGF was increased in the range from 0.1 to 1,000 µM in a cotinine-pegaptanib concentration-dependent manner. This was similar to a concentration dependent mannered binding ability to VEGF of bevacizumab, an anti-VEGF antibody.

Experimental Example 9: Reactivity of Cotinine-Abciximab/Anti-Cotinine IgG Complex (9-1) Enzyme-Linked Immunosorbent Assay to Determine Reactivity of Cotinine-Abciximab/Anti-Cotinine IgG Complex, Cotinine-Abciximab, and Abciximab Reactivity of the complex to integrin alpha2b beta3 was measured by using 0.001 nM to 1,000 nM abciximab and cotinine-abciximab. 1 µM of an anti-cotinine IgG antibody was used.

Specifically, 100 ng of integrin alpha2b beta3 dissolved in 20 µL of a metal buffer (25 mM Tris-Cl, 137 mM NaCl, 1 mM $MgCl_2$, 1 mL $CaCl_2$, 1 mM $MnCl_2$ and 1 mM KCl; pH 7.5) was added to each well, and then cultured at 37° C. for two hours to coat micro titer plate wells of a half area of the 96-wells with integrin alpha2 beta3. The wells were blocked at 37° C. for one hour with 150 µL PBSB (including 3% of BSA in PBS). Abciximab/cotinine, and abciximab, which include or exclude the anti-cotinine antibody, were adjusted to various concentrations in 3% of PBSB, then applied to each well in a final volume of 50 µL. The plate was cultured at 37° C. for one hour, and washed three times with PBS containing 0.05% of Tween 20 (PBST). Then, the plate was treated with an anti-human Fc-HRP antibody to detect cotinine-abciximab/anti-cotinine IgG antibody complex, followed by treating an anti-human Fab-HRP to detect Cotinine-abciximab and abciximab. The plate was cultured at 37° C. for 45 minutes, and washed four times with 0.05% of PBS-T. After that, each well was cultured with 100 µL of ABTS substrate solution at 37° C. for 30 minutes and then the absorbance was measured at 405 nm. The result was shown in FIG. 18.

Figure 18:
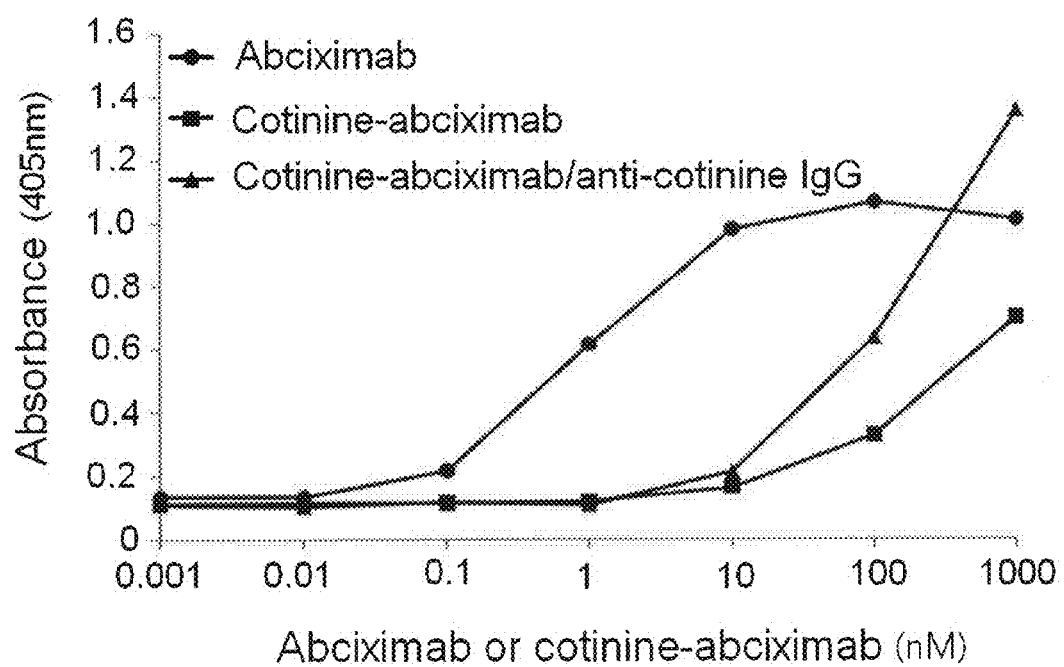
FIG. 18 is a graph showing reactivities of abciximab, an abciximab/cotinine conjugate, and a cotinine-abciximab/anti-cotinine IgG complex to integrin α2b β3.

As shown in FIG. 18, it can be determined that the cotinine-abciximab/anti-cotinine antibody complex of the present invention maintained the same reactivity as those of abciximab to integrin alpha 2b beta3.

(9-2) Specific Binding Test of Cotinine-abciximab/Anti-Cotinine Antibody Complex to Human Platelet Human platelet activated by 0, 0.1 and 1 µM of an anti-cotinine antibody, was treated with 0, 5, and 50 nM of cotinine-abciximab, and an anti-human Fc-FITC (Theremo Fisher Scientific, USA), which was diluted at a ratio of 1:75 to the platelet, and cultured for 20 minutes. Subsequently, the resulting cells were analyzed by flow cytometry assay in the same manner as Experimental Example 8.

Specifically, 1.5 mL of blood was added to a 5 mL vacutainer tube including 0.84 mL of acid-citric acid-dextrose (ACD) and 10 mL of EDTA. The blood was transferred to a centrifuge tube and rotated at 250×g for 10 minutes at a room temperature. Platelet rich plasma (PRP) was transferred to a new tube and rotated at a room temperature for 10 minutes at 1500 rpm. Supernatant was removed therefrom, and the platelet was washed with 1 mL of Tyrode's buffer (137 mM NaCl, 2.7 mM KCl, 2 mM MgCl, 0.5 mM $NaH_2PO_4$, 5 mM glucose, 10 mM HEPES and 0.2% BSA; pH 7.4). After centrifuging at 1500 rpm for 7 minutes, the supernatant was removed, and then pellet was resuspended in 300 μL of a metal buffer (25 mM Tris-Cl, 137 mM NaCl, 1 mM $MgCl_2$, 1 mL $CaCl_2$, 1 mM $MnCl_2$ and 1 mM KCl; pH 7.5) supplemented with 0.1% of BSA. 50 μL of the PRP suspended solution thus obtained was applied to FACS analysis. 25 μL of abxicimab-cotinine in various concentrations, and 25 μL of the anti-cotinine antibody or Synagis® were applied in the metal buffer supplemented with 0.1% of BSA for 45 minutes at a room temperature. After washing twice with the same buffer, anti-human Fc-FITC, as a secondary antibody, at a concentration of 1 μg/mL was applied to 50 μL of the metal buffer supplemented with 0.1% of BSA, and the samples were maintained at the room temperature under the dark condition. Subsequently, the obtained cells were washed with the same buffer twice, and then resuspended with 100 μL of PBS. Flow cytometry analysis was performed for two kinds of cell lines using a FACScan fluorescence activated cell analyzer (BD Biosciences). The result was shown in FIG. 19.

As a negative antibody control group, Synagis®, which was treated with the same concentration to the anti-cotinine antibody, was used, and as a positive control group, abciximab (0 nM, 5 nM and 50 nM) was used.

Figure 19:
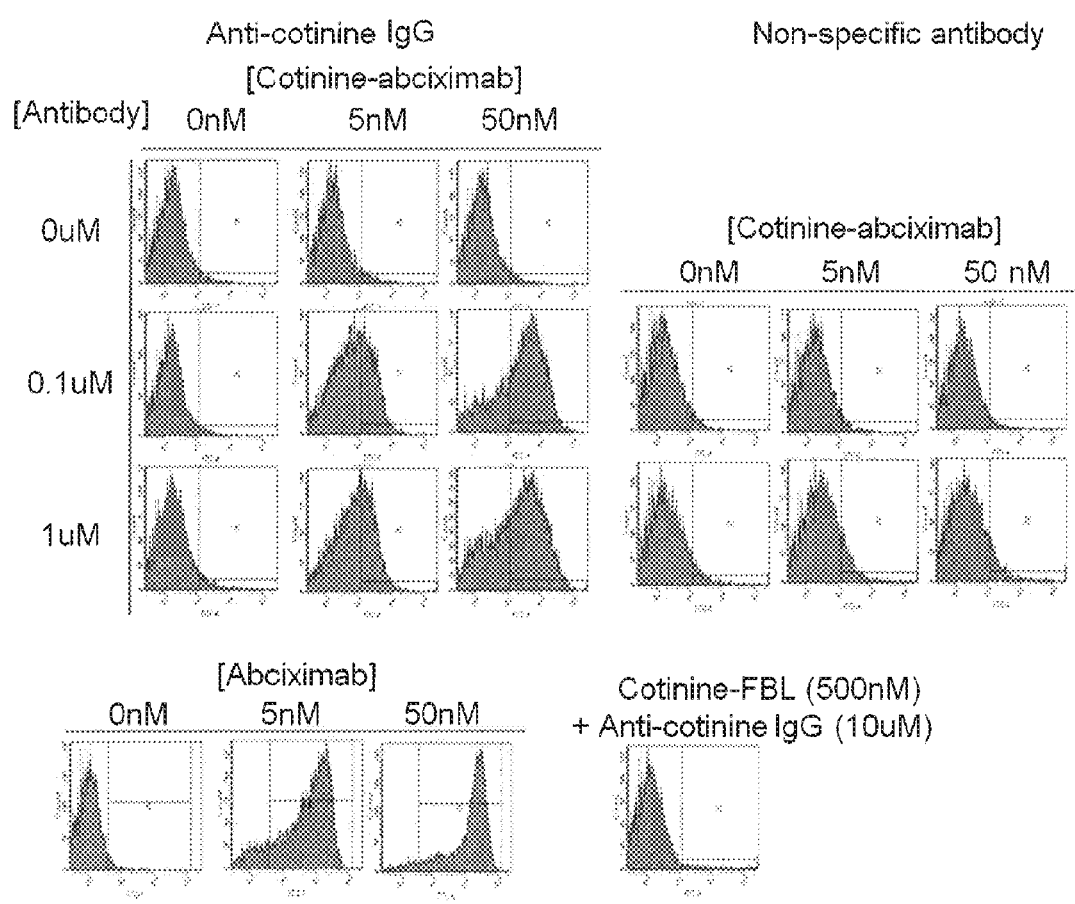
FIG. 19 shows a test result of a binding ability of the cotinine-abciximab/anti-cotinine IgG complex to platelets.

As shown in FIG. 19, cotinine-abciximab/anti-cotinine antibody complex maintained the same reactivity to platelet as abciximab, and it can be understood that the binding degree of the complex was increased as cotinine-abciximab or the anti-cotinine antibody concentration was increased. Contrarily, FBL-cotinine treated with the anti-cotinine antibody (10 μM) did not bind to the platelet.

Experimental Example 10: Reactivity of Cotinine-Insulin/Anti-Cotinine Antibody Complex ($10^{-1}$) Specific Binding Test of Cotinine-Insulin/Anti-Cotinine Antibody Complex to MCF-7 and SK-Br-3 Cell Specifically, SK-Br-3 cells or MCF-7 cells (insulin receptor positive breast cancer cell line)(ATCC, USA)($1×10^6$/reaction) were washed three times with FACS buffer (PBS, 1% FBS and 0.02% sodium azide). 25 μL of cotinine-insulin in a various concentrations (0-5,000 nM), and 25 μL of an anti-cotinine antibody (1,000 nM) or 25 μL of Synagis® (1,000 nM) were applied in a FACS buffer at a room temperature for 45 minutes. In this case, Synagis® was used as a negative antibody control group. After washing twice with FACS buffer, 1 μg/mL of an anti-human Fc-FITC, a second antibody, was applied in 50 μL of FACS buffer, and then maintained under the dark condition at a room temperature for 30 minutes. Subsequently, the cells were washed with FACS buffer twice, and resuspended in 100 μL PBS. Two kinds of cell lines were subjected to fluorescence analysis using flow cytometry analysis by FACScan fluorescence activated cell analyzer (BD Biosciences). The result was shown in FIG. 20A.

In contrast, the cells were cultured using 5,000 nM of the cotinine-insulin/anti-cotinine antibody complex, and a cotinine-negative peptide/anti-cotinine antibody complex in the same manner as described in above using anti-human Fc-FITC, and then subjected to flow cytometry analysis. In this case, a cotinine-FBL conjugate (SEQ ID No: 19) which is a follicular B lymphocyte binding peptide, a cotinine-A14 conjugate (SEQ ID No: 20) which is an apelin receptor binding peptide, and a cotinine-F13A conjugate (SEQ ID No: 21) (ST Pharm, Korea) were used as cotinine-negative peptide conjugates. The result was shown in FIG. 20B.

Figure 20:
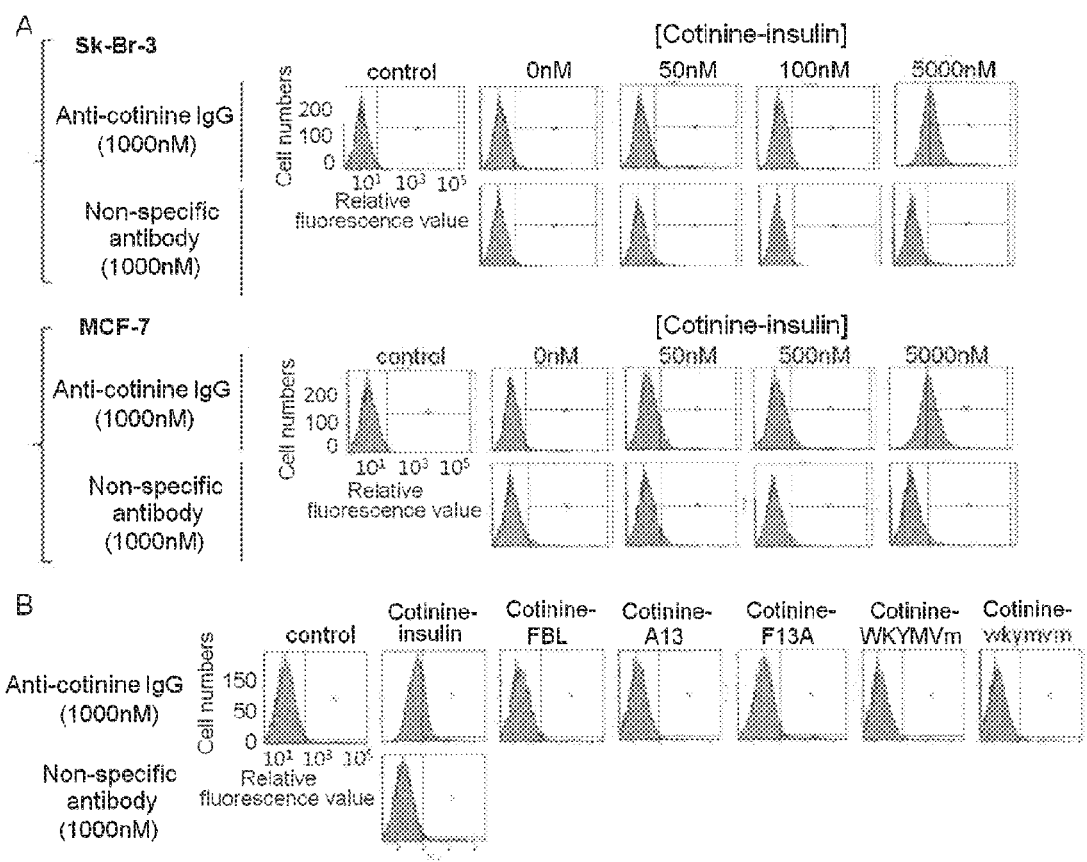
FIG. 20 shows a test result of a binding ability of a cotinine-insulin/anti-cotinine antibody complex to a MCF-7 cell and a SK-Br-3 cell.

As shown in FIG. 20, it can be understood that the insulin-cotinine/anti-cotinine antibody complex maintains the binding ability of insulin to a receptor, since the complex successfully binds to a cell expressing an insulin receptor.

(10-2) CDC Analysis of Cotinine-Insulin/Anti-Cotinine Antibody Complex

To perform CDC analysis, a cotinine-insulin/anti-cotinine antibody complex was tested using a cell viability indicator WST-1 (Takara).

Specifically, MCF-7 cells (ATCC, USA) which express an insulin receptor, was washed with an analysis medium (DMEM, 1% FBS) and diluted to $1×10^5$ mL 100 μL of the cell suspension solution was applied to each well in a sterilized 96-well tissue culture plate and cultured in a 5% $CO_2$ incubator at 37° C. for overnight so that the cells were adhered to the well. The analysis medium was removed from the cells, and then a set of well including 25 μL cotinine-insulin, 25 μL of the anti-cotinine antibody in various concentrations (0, 0.1, and 1 μM), and 50 μL of 1/12 human complement dilution was cultured in a 5% $CO_2$ incubator at 37° C. to facilitate human complement-mediated cell lysis. After overnight culture, 10 μL of WST-1 (Takara) was added to each well, and cultured at 37° C. for an additional three hours, and then the absorbance was measured at 450 nm. 1% Triton X-100 and medium were applied to high-control and low-control cells with human serum. Also, the cotinine-insulin/anti-cotinine antibody complex was applied to the wells with human serum without cells as a supplement control group. Each analysis was repeated three times and the results are shown in FIG. 21. A high-control group refers to the case where 100% of cells were dead by 1% of Triton X-100, and a low-control group refers to the case where cell death was not induced by complement, meanwhile a buffer control group (bf control group) refers to the case where the difference in the results were measured depending on the buffer regardless of other conditions.

Figure 21:
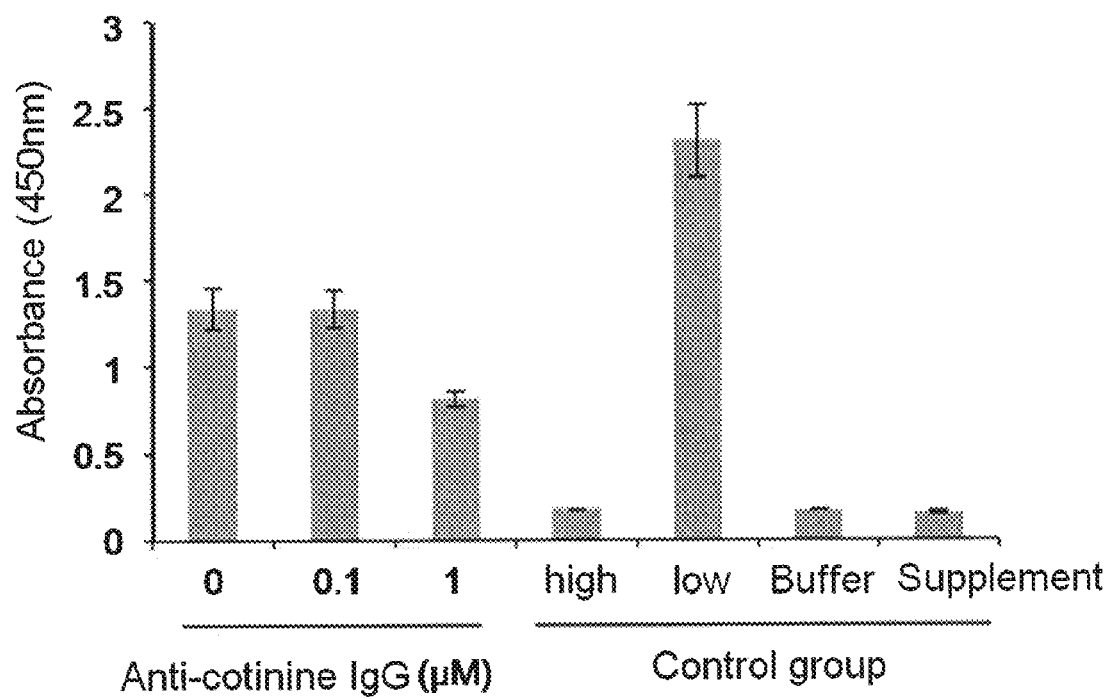
FIG. 21 shows an analysis result of a complement-mediated toxicity of the cotinine-insulin/anti-cotinine antibody complex.

As shown in FIG. 21, it can be understood that the cotinine-insulin/anti-cotinine antibody complex of the present invention maintains CDC of the anti-cotinine antibody which serves as a cytotoxic agent specific for an insulin receptor which overexpresses breast cancer cells.

Experimental Example 11

Figure 23:
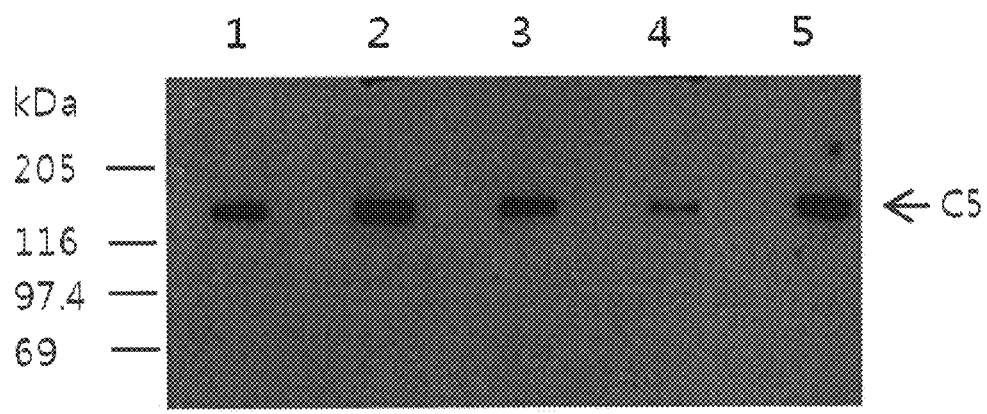
FIG. 23 shows results obtained by performing affinity chromatography using protein A agarose to purify an ScFv antibody specific to a human complement C5 from a cell culture medium.

ScFv was combined using only sequences of $V_H$ and $V_L$ obtained from an amino acid sequence of immunoglobulin eculizumab (U.S. Pat. No. 6,355,245 B 1) having a binding ability to human complement component 5 (C5), and then the combined ScFv was located in a first scFv of cotinibody (ScFv of an antibody which binds to cotinine). A vector thus obtained was transformed into a 293F cell line to express a protein. Then, affinity chromatography using protein A agarose was performed to purify an antibody from the cell culture. SDS-PAGE was performed using 20 μL of human serum, which was diluted in 1/10, 1/20, 1/40 and 1/80 (lanes 1, 2, 3, and 4), and 100 ng of the purified human complement component C5 (lane 5), and then the proteins obtained from the electrophoresis were transferred to a nitrocellulose membrane. A human complement component C5-cotinibody protein was diluted in a 5% skim milk in Tris-buffered saline solution to yield a concentration of 2 μg/mL, and allowed to react for 16 hours at 4° C. while the membrane remained in contact with the samples. The membrane was washed with a TBS solution containing 0.2% of Tween 20, and allowed to react with a solution in which horseradish peroxidase bound cotinine was diluted to 1/1,000 for 2 hours at a room temperature. Then, the resulting membrane was washed with TBS containing 0.2% of Tween 20, and treated with a chemiluminescent material and then sensitized to a film. It was determined that human complement component C5-cotinibody selectively binds to human complement component C5 (FIG. 23).

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A complex in which an anti-cotinine antibody is bound to a conjugate of cotinine and a binding material,
   wherein the binding material is selected from the group consisting of a peptide, an aptamer, an antibody, and a hormone, and
   wherein the binding material is linked to the cotinine via a PEG linker or an amino C6 linker.

2. The complex of claim 1, wherein the binding material is selected from the group consisting of WKYMVm-NH$_2$ peptide, AS1411 aptamer, pegaptanib, abciximab and insulin.

3. The complex of claim 1, wherein the conjugate is bound to an antigen binding site of the anti-cotinine antibody.

4. The complex of claim 1, wherein the anti-cotinine antibody is selected from the group consisting of the antibody; an antibody fragment selected from Fab, ScFv and domain antibodies; and a fusion protein comprising the antibody or the antibody fragment as a component.

* * * * *

SEQUENCE LISTING

<160> NUMBER OF SEQ ID NOS: 21

<210> SEQ ID NO 1
<211> LENGTH: 6
<212> TYPE: PRT
<213> ORGANISM: Artificial Sequence
<220> FEATURE:
<223> OTHER INFORMATION: WKYMVm-NH2 peptide

<400> SEQUENCE: 1

Trp Lys Tyr Met Val Met
 1               5

<210> SEQ ID NO 2
<211> LENGTH: 6
<212> TYPE: PRT
<213> ORGANISM: Artificial Sequence
<220> FEATURE:
<223> OTHER INFORMATION: wkymvm-NH2 peptide

<400> SEQUENCE: 2

Trp Lys Tyr Met Val Met
 1               5

<210> SEQ ID NO 3
<211> LENGTH: 29
<212> TYPE: DNA
<213> ORGANISM: Artificial Sequence
<220> FEATURE:
<223> OTHER INFORMATION: AS1411 DNA aptamer

<400> SEQUENCE: 3
dttggtggtg gtggttgtgg tggtggtgg                                    29

<210> SEQ ID NO 4
<211> LENGTH: 27
<212> TYPE: DNA
<213> ORGANISM: Artificial Sequence
<220> FEATURE:
<223> OTHER INFORMATION: CRO26 DNA aptamer

<400> SEQUENCE: 4
dcctcctcct cctctcctc ctcctcc                                       27

<210> SEQ ID NO 5
<211> LENGTH: 27
<212> TYPE: RNA
<213> ORGANISM: Artificial Sequence
<220> FEATURE:
<223> OTHER INFORMATION: pegaptanib RNA aptamer
<220> FEATURE:
<221> NAME/KEY: modified_base
<222> LOCATION: (1)..(27)

<223> OTHER INFORMATION: C and U are 2'-fluoro, G and A are 2'-methyl,
    wherein A4 and A5 are 2'-hydroxyl

<400> SEQUENCE: 5
cggaaucagu gaaugcuuau acauccg         27

<210> SEQ ID NO 6
<211> LENGTH: 107
<212> TYPE: PRT
<213> ORGANISM: Artificial Sequence
<220> FEATURE:
<223> OTHER INFORMATION: Synthetic insulin

<400> SEQUENCE: 6

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Arg Arg Glu Ala Glu Asp Leu Gln Val Gly Gly
    50                  55                  60

Val Leu Gly Gly Gly Pro Gly Ala Gly Ser Leu Gln Pro Leu Ala Leu
65                  70                  75                  80

Glu Gly Ser Leu Gln Lys Arg Gly Ile Val Glu Gln Cys Cys Thr Ser
                85                  90                  95

Ile Cys Ser Leu Gln Leu Glu Asn Tyr Cys Asn
            100                 105

<210> SEQ ID NO 7
<211> LENGTH: 48
<212> TYPE: DNA
<213> ORGANISM: Artificial Sequence
<220> FEATURE:
<223> OTHER INFORMATION: forward primer for anti-cotinine rabbit/human
    chimeric antibody light chain

<400> SEQUENCE: 7
acttaagctt gcgccaccat gggctggtcc tgcatcatcc tgttcctg         48

<210> SEQ ID NO 8
<211> LENGTH: 24
<212> TYPE: DNA
<213> ORGANISM: Artificial Sequence
<220> FEATURE:
<223> OTHER INFORMATION: reverse primer for anti-cotinine rabbit/human
    chimeric antibody light chain

<400> SEQUENCE: 8
gcaagctcta gactagcact cgcc         24

<210> SEQ ID NO 9
<211> LENGTH: 49
<212> TYPE: DNA
<213> ORGANISM: Artificial Sequence
<220> FEATURE:
<223> OTHER INFORMATION: forward primer for anti-cotinine rabbit/human
    chimeric antibody heavy chain

<400> SEQUENCE: 9
acatcggcta gccgccacca tgggctggtc ctgcatcatc ctgttcctg         49

<210> SEQ ID NO 10

<211> LENGTH: 24
<212> TYPE: DNA
<213> ORGANISM: Artificial Sequence
<220> FEATURE:
<223> OTHER INFORMATION: reverse primer for anti-cotinine rabbit/human
      chimeric antibody heavy chain

<400> SEQUENCE: 10
gagctcggat cccttgccgg ccgt                                          24

<210> SEQ ID NO 11
<211> LENGTH: 48
<212> TYPE: DNA
<213> ORGANISM: Artificial Sequence
<220> FEATURE:
<223> OTHER INFORMATION: forward primer for light chain variable region
      from anti-cotinine rabbit scFV

<400> SEQUENCE: 11
atcctgttcc tggtggccac cgccaccggc gagctcgatc tgacccag                48

<210> SEQ ID NO 12
<211> LENGTH: 24
<212> TYPE: DNA
<213> ORGANISM: Artificial Sequence
<220> FEATURE:
<223> OTHER INFORMATION: reverse primer for light chain variable region
      from anti-cotinine rabbit scFV

<400> SEQUENCE: 12
taggatctcc agctcggtcc ctcc                                          24

<210> SEQ ID NO 13
<211> LENGTH: 48
<212> TYPE: DNA
<213> ORGANISM: Artificial Sequence
<220> FEATURE:
<223> OTHER INFORMATION: forward primer for heavy chain variable region
      from anti-cotinine rabbit scFV

<400> SEQUENCE: 13
atcctgttcc tggtggccac cgccaccggc cagtcggtga aggagtcc                48

<210> SEQ ID NO 14
<211> LENGTH: 24
<212> TYPE: DNA
<213> ORGANISM: Artificial Sequence
<220> FEATURE:
<223> OTHER INFORMATION: reverse primer for heavy chain variable region
      from anti-cotinine rabbit scFV

<400> SEQUENCE: 14
tgaagagatg gtgaccaggg tgcc                                          24

<210> SEQ ID NO 15
<211> LENGTH: 24
<212> TYPE: DNA
<213> ORGANISM: Artificial Sequence
<220> FEATURE:
<223> OTHER INFORMATION: forward primer for light chain constant region
      from human

<400> SEQUENCE: 15
gagctcggat cccttgccgg ccgt                                          24

<210> SEQ ID NO 16
<211> LENGTH: 24

```
<212> TYPE: DNA
<213> ORGANISM: Artificial Sequence
<220> FEATURE:
<223> OTHER INFORMATION: reverse primer for light chain constant region
      from human

<400> SEQUENCE: 16
gcaagctcta gactagcact cgcc                                            24

<210> SEQ ID NO 17
<211> LENGTH: 30
<212> TYPE: DNA
<213> ORGANISM: Artificial Sequence
<220> FEATURE:
<223> OTHER INFORMATION: forward primer for heavy chain constant region
      from human

<400> SEQUENCE: 17
gtcaccatct cttcagcctc caccaagggc                                      30

<210> SEQ ID NO 18
<211> LENGTH: 30
<212> TYPE: DNA
<213> ORGANISM: Artificial Sequence
<220> FEATURE:
<223> OTHER INFORMATION: reverse primer for heavy chain constant region
      from human

<400> SEQUENCE: 18
gagctggaga tcctacggac cgtggccgcc                                      30

<210> SEQ ID NO 19
<211> LENGTH: 16
<212> TYPE: PRT
<213> ORGANISM: Artificial Sequence
<220> FEATURE:
<223> OTHER INFORMATION: FBL peptide

<400> SEQUENCE: 19

Glu Tyr Val Asn Cys Asp Asn Leu Val Gly Asn Cys Val Ile Arg Gly
 1               5                  10                  15

<210> SEQ ID NO 20
<211> LENGTH: 12
<212> TYPE: PRT
<213> ORGANISM: Artificial Sequence
<220> FEATURE:
<223> OTHER INFORMATION: A13 peptide

<400> SEQUENCE: 20

Gln Arg Pro Arg Leu Ser His Lys Gly Pro Met Pro
 1               5                  10

<210> SEQ ID NO 21
<211> LENGTH: 13
<212> TYPE: PRT
<213> ORGANISM: Artificial Sequence
<220> FEATURE:
<223> OTHER INFORMATION: F13A peptide

<400> SEQUENCE: 21

Gln Arg Pro Arg Leu Ser His Lys Gly Pro Met Pro Ala
 1               5                  10
```